US006994855B1

(12) United States Patent  
Foster et al.

(10) Patent No.: US 6,994,855 B1
(45) Date of Patent: Feb. 7, 2006

(54) S. AUREUS FIBRINOGEN BINDING PROTEIN GENE

(75) Inventors: Timothy James Foster, Dublin (IE); Damien Leo McDevitt, Dublin (IE)

(73) Assignee: The Provost Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 1017 days.

(21) Appl. No.: 09/679,643

(22) Filed: Oct. 5, 2000

Related U.S. Application Data

(62) Division of application No. 09/421,868, filed on Oct. 19, 1999, now Pat. No. 6,177,084, which is a division of application No. 08/293,728, filed on Aug. 22, 1994, now Pat. No. 6,008,341.

(51) Int. Cl.
*A61K 39/40* (2006.01)
(52) U.S. Cl. ............................... 424/165.1; 530/387.1; 530/388.1; 424/130.1; 424/141.1; 424/150.1
(58) Field of Classification Search .............. 530/387.1, 530/388.1; 424/130.1, 141.1, 150.1, 165.1
See application file for complete search history.

(56) References Cited

OTHER PUBLICATIONS

Homonylo et al. Infection and Immunity. 1993. 61(6): 2479-2485.*
McDevitt et al. Molecular Microbiology. Jan. 1994. 11(2): 237-248.*
Signas et al. Proc. Natl. Acad. Sci., USA, 1989, 86: 699-703.*
Jonsson et al. Eur. J. Biochem. 1991, 202: 1041-1048.*
Amann, E. and Brosius, J. (1985). "'ATG Vectors' for regulated high level expression of cloned genes in *Esherichia coli*." Gene 40, 183-190.
Baier, R.E. (1977). "The organisation of blood components near interfaces." Ann N.Y. Acad Sci 283:17-36.
Boden, M.K., and Flock, J.I. (1989). "Fibrinogen-binding protein/clumping factor from *Staphylococcus aureus*." Infect. Immun. 57: 2358-2363.
Boden, M.K., and Flock, J.I. (1992). "Evidence for three different fibrinogen binding proteins with unique properties from *Staphylococcus aureus* strain Newman." Microbiol. Pathogen., 12(4), 289-298.
Boden, M.K., and Flock, J.I. (1994). "Cloning and characterization of a gene for a 19kDa Fibrinogen-binding protein from *Staphylococcus aureus*." Molec. Microbiol. 12(4), 599-606.
Chhatwal, G.S., Albohn, G. and Blobel, H. (1987). "Interaction between fibronectin and purified staphyococcal clumping factor." FEMS Microbiol. Lett. 44, 147-151.

Cheung, A. and Fischetti, V.A. (1990). "Role of surface proteins in staphylococcal adherence to catheters in vitro." J. Infect. Dis. 161, 1177-1186.
Cheung, A.L. Kirshnan, N., Jaffee, E.A. and Fischetti, V.A. (1991). "Fibrinogen acts as a bridging molecule in the adherence of *Staphylococcus aureus* to cultured human endothelial cells." J. Clin. Invest. 87, 2236-2245.
Cheung, A.L., Yeaman, M.R. Sullam,, P.M., Witt, M.D. and Bayer A.S. (1994). "Role of the sar locus of *Staphylococcus aureus* in induction of endocarditis in rabbits." Infect. Immun. 62, 1719-1725.
Cottonaro, C.N. Roohk, H.V., Shimica, G. and Sperling, D.R. (1981). "Quantitation and characterization of competitive protein binding to polymers." Trans Am. Soc. Artif. Inter. Organs 27:391-395.
Davidson, V.E., and Sandford, B.A. (1982). "Factors influensing adherence of *Staphylococcus aureus* to Influenza A virus-infected cell cultures." Infect. Immun, 37:946-955.
Duthie, E.S. (1954). "Evidence of two forms of staphlococcal coagulase." J. Gen. Microbiol. 10:427-436.
Espersen, F., Clemmensen, I., and Barkholt, V. (1985). "Isolation of *Staphylococcus aureus* clumping factor." Infect. Immun. 49:700-708.
Garrison, P.K. and Freedman, L.R. (1970). "Experimental endocarditis. 1. Staphylococcal endocarditis in rabbits resulting from placement of a polyethylene catheter in the right side of the heart." Yale J. Biol. Med. 42, 394-410.
Guan, K. and J.E. Dixon. (1991). "Eukaryotic proteins expressed in *Escherichia coli*; An improved thrombin cleavage and purification procedure of fusion proteins with glutathione S-transverse." Anal. Biochem. 192, 262-267.
Hawiger, J.S., Hammond, D.K., Timmons, S. and Budzynski, A.Z. (1978). Interaction of human fibrinogen with staphylococci: presence of a binding region on a normal and abnormal fibrinogen variants and fibrinogen Blood 51:799-812.
Hawiger, J.S., Timmons, S., Strong, D.D. Cottrell, B.A., Riley, M., and Doolittle, R.F. (1982). "Identification of a region of human fibrinogen interacting with staphylococcal clumping factor." Biochemistry 21:1407-1413.
Herrmann, M., Lai, Q.J., Albrecht, R.M., Mosher, D.F. and Proctor, R.A. (1993). "Adhesion of a *Staphylococcus aureus* to surface-bound platelets: role of fibrinogen/fibrin and platelet integrins." J. Infect. Dis. 167, 312-322.

(Continued)

*Primary Examiner*—Jennifer E. Graser
(74) *Attorney, Agent, or Firm*—B. Aaron Schulman; Stites & Harbison, PLLC

(57) ABSTRACT

The invention relates to the isolation of the fibrinogen binding protein gene from *Staphylococcus aureus* and to the use of the fibrinogen binding protein and antibodies generated against it for wound healing, blocking adherence to indwelling medical devices, immunization or diagnosis of infection.

9 Claims, 13 Drawing Sheets

OTHER PUBLICATIONS

Figure 1:
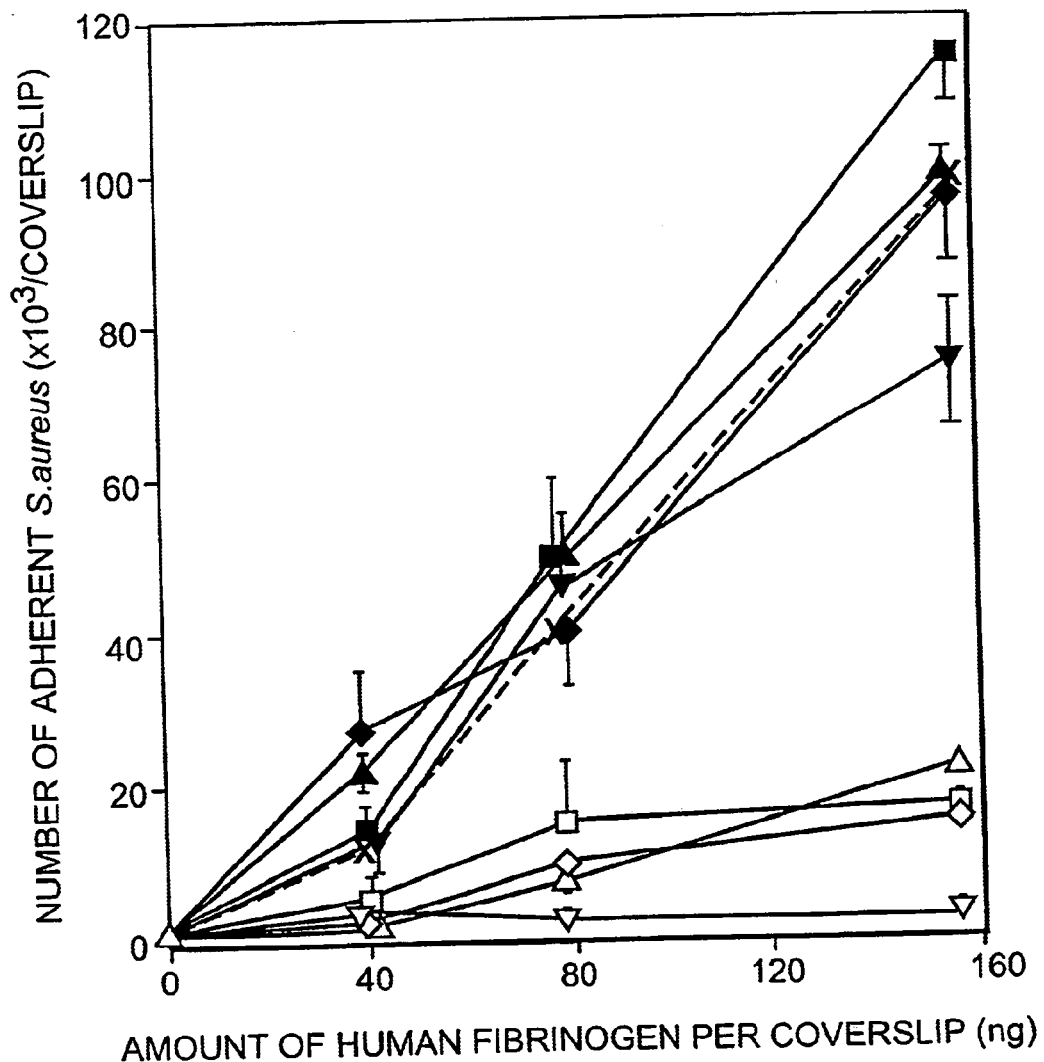

Homonylo McGavin, M., Krajewska-Pietrasik, D., Ryden, C. and Hook, M. (1993). "Identification of a *Staphylococcus aureus* extracellular matrix-binding protein with broad specificity." Infect. Immun. 61, 2479-2485.

Kochwa, S., Litwak, R.S. Rosenfield, R.E. and Leonard, E.F. (1977). "Blood elements at foreign surfaces: a biochemical approach to study the absorption of plasma proteins." Ann. NY Acad Sci 238, 27-49.

Kristinsson, K.G. (1989). "Adherence of staphylococci to intravascular catheters." J. Med. Microbiol. 28:249-257.

Lantz, M.S., Allen, R.D., Bounelis, P., Switzalski, L.M. and Hook, M. (1990). *Bacteriodes gingivatis* and *Bacteriodes intermedius* recognize different sites on human fibrinogen. J. Bacteriol. 172, 716-726.

Lee, C.Y., Buranem, S.L. and Ye, Z-H. (1991). Construction of single copy integration vectors for *Staphylococcus aureus*. Gene 103:101-105.

McDevitt, D., Vaudaux P. and Foster, T.J. (1992). "Genetic evidence that bound coagulase of *Staphylococcus aureus* is not clumping factor." Infect. Immun. 60:1514-1523.

McDevitt, D., Francois, P., Vaudaux, P. and Foster T.J. (1994). Molecular characterization of the fibrinogen receptor (clumping factor) of *Staphylococcus aureus*. Molec, Microbiol. 11, 237-248.

Maki, D.G. (1992). "Infections associated with intravascular lines." In *Current topics in infectious diseases*. vol. 3 Remington J.S., and Swartz, M.N. (eds.). McGraw Hill, New York, pp. 309-363.

Nowicki, B., Rhen, M., Vaisanen-Rhen, V., Pere, A. and Korhonen, T.K. (1984). "Immunofluorescence study of fimbrial phase variation in *Escherichia coli* KS71." J. Bacteroil. 160, 691-695.

Patel, A.H., Nowlan, P. Weavers, E.D. and Foster, T.J. (1987). "Virulence of protein A-deficient and alpha toxin-deficient mutants of *Staphylococcus aureus* isolated by allelic-replacement." Infect. Immun. 55,3103-3110.

Patti, J.M., Jonsson, H., Guss, B., Switalski, L.M., Wiberg, K., Lindberg, M. and Hook M. (1992). "Molecular Characterization and expression of a gene encoding a *Staphylococcus aureus* collagent adhesin." J. Biol. Chem. 267, 4766-772.

Schneewind, O., Mihaylova, D. and Model, P. (1993). "Cell wall sorting signals in surface proteins of Gram-positive bacteria." EMBO J. 12, 4803-4811.

Signas, C., Raucci, G., Jonsson, K., Lindgren, P.E., Anantharamaiah, G.M., Hook, M. and Lindberg, M. (1989). Nucleotide sequence of the gene for a fibronectin-binding protein from *Staphylococcus aureus*: use of this peptide sequence in the synthesis of biologically active peptides. Proc. Natl. Acad. Sci. USA 86:699-703.

Switalski, L.M. (1976). "Isolation and purification of staphylococcal clumping factor." In *Staphylococci and staphylococcal diseases*. Jeljaszewicz, J. (ed.) Gustav Fischer Verlag, Stuttgart, pp. 413-425.

Tomich, P.K., An, F.Y, and Clewell, D.B. (1980). Properties of erythromycin inducible transposon Tn917 in *Streptococcus faecalis*. J.Bacteroil. 141, 1366-1374.

Usui, Y. (1986). "Biochemical properties of fibrinogen binding protein (clumping factor) of the staphylococcal cell surface." 26L Bakt. Myg. A262, 287-297.

Vaudaux, P. Pittet, D. Haeberli, A., Huggler, E., Hydegger, U.E., Lew, D.P. and Waldvogel, F.A. (1989). "Host factors selectively increase staphylococcal adherence on inserted catheters. A role for fibronectin and fibrinogen or fibrin." J. Infect. Dis. 160, 865-875.

Vaudaux, P., Proctor, R.A., McDevitt, D., Foster, T.J., Lew, D.P., Wabers, H. and S. Cooper. (1991). "Use of adherence defective mutants of *Staphylococcus aureus* (SA) to identify adherence promoting proteins deposited from profusing blood . . . . " Program Abstr. 31st Intersci. Conf. Antimicrobiol. Agents Chemother., abst 1068.

Vaudaux, P., Pittet, D., Haeberli, H. Lerch, P.G., Morgenthaler, J.J., Proctor, R.A., Waldvogel, F.A. and Lew, D.P. (1993). "Fibronectin is more active than fibrin or fibrinogen in promoting *Staphylococcus aureus* adherence to inserted intravascular devices." J. Infect. Dis. 167, 633-641.

Yanisch-Perron, C., Veira, J.C. and Messing, J. (1985). "Improved M13 phage cloning vectors and host strains:" nucleotide sequences of the M13mp18 and pUC19 vectors. Gene 33:103-119.

Yougman, P. (1985). "Plasmid vectors for recovering and exploiting Tn917 transpositions in Bacillus and other Gram-positives." In Plasmids: a Practical approach. Hardy, K. (ed.), IRL Press, Oxford, pp. 79-103.

\* cited by examiner

```
                                                                                                    81
AAAAAATGTTGCAATCAAATCGTACGTTGTCGTTTGTAATTCTTAAAATAGCAATAAATGTTTGTTTAGTAAAGTATTATTGTGGATAATAAATATCGATACAA  191
                              -35                                    -10            RBS
ATTAATTCCTATAATGCAATTTAGTGTATAATTCCATTAACAGAGATAAATATATCTTTAAAGGGTATATAGTTAATATAAAATGACTTTTAAAAAGAGGGAATAAA  301
ATGAATATGAAGAAAAAAGAAAAACACGGCAATTCGGAAAAAAATCGATTGGGCGTCGCTTCAGTGCTTGTAGTAGGCGTTAATCGGTTTTGGACTACTCAGCAGTAAAGAAGC  411
M  N  M  K  K  K  E  K  H  A  I  R  K  K  S  I  G  V  A  S  V  L  V  G  T  L  I  G  F  G  L  L  S  S  K  E  A   37
     A →
     S →
AGATGCAAGTGAAACTGTTACGCAATCTGATAGCGCAAGAAAGTAACGAAGAACAAAGTGCGCCAAAATCCAGCACAATCATCAACAATGCAACTACGAAGAA  521
D  A  S  E  N  S  V  T  Q  S  D  S  A  S  N  E  S  K  S  N  D  S  S  S  V  S  A  A  P  K  T  D  D  T  N  V  S   74
GTGATACTAAAACATCGTCAAACACTAATAATGCCAACGAGTGTGGGCAAATCCAGCACACAAGACACAATCATCAACAAATGCAACTACGAAGAA  631
D  T  K  T  S  S  N  T  N  N  G  E  T  S  V  A  Q  N  P  A  Q  Q  E  T  T  Q  S  S  T  N  A  T  T  E  E        110
ACGCCGGTAACTGGTGAAGCTACTACTACGACGAATCAAGGCCAACACTAATCAAGACAATACAAGCCGAGGAATTAGTGAATCAAACAAGTAA  741
T  P  V  T  G  E  A  T  T  T  T  N  Q  A  N  T  P  A  T  T  Q  S  S  N  T  N  A  E  E  L  V  N  Q  T  S  N      147
TGAAACGACTTTTAATGATACTAATACAGTATCATCTGTAAATTCACCTCAAATGTTCAACAACGCAAGATACTTCAACTGAAGCAACAC  851
E  T  T  F  N  D  T  N  T  V  S  S  V  N  S  P  Q  N  S  T  N  A  E  N  V  S  T  T  Q  D  T  S  T  E  A  T  P   184
CTTCAAACAATGAATCAGCTCCACAGAGTACAGATGCAAGTAATAAAGATGTAGTTAATCAAGGCGGTAATACAAGTGCGCCTAGAATGAGAGCATTAGTTTCGGCA  961
S  N  N  E  S  A  P  Q  S  T  D  A  S  N  K  D  V  V  N  G  A  V  N  T  S  A  P  R  M  R  A  F  S  L  A  A      220
 PSTI
GTAGCTGCAGATGCACCGGCAGCTGGCACAGATATTACGAATCAGTTGACGAATGTGACAGTTGGTATTGACTCTGGTACGACTGTGTATCCGCACCAAGCAGGTTATGT  1071
V  A  A  D  A  P  A  A  G  T  D  I  T  N  Q  L  T  N  V  T  V  G  I  D  S  G  T  T  V  Y  P  H  Q  A  G  Y  V   257
```

FIG. 2A-1

```
CAAACTGAATTATGTTTTTCAGTGCCTAATTCTGTGTTAAAGGTGACACATTCAAAATAACTGTACCTAAAGAATAAACTTAAATGGTGTAACTTCAACTGCTAAAG    1181
 K  L  N  Y  V  F  S  V  P  N  S  V  L  K  G  D  T  F  K  I  T  V  P  K  E  L  N  L  N  G  V  T  S  T  A  K  V    294

TGCCACCAATTATGCTGGAGATCAAGTATTGGCAAATGGTGTAATCGATAGTGATGGTAATGTTATTTATACATTTACGACTGATGTTTATAATACTAAAGATGATGTAAAA    1291
 P  P  I  M  A  G  D  Q  V  L  A  N  G  V  I  D  S  D  G  N  V  I  Y  T  F  T  D  Y  V  N  T  K  D  D  V  K    330

GCAACTTGACCATGCCCGCTTATATTGACCCTGAAAATGTTAAAAAGACAGGTAATGTGACATTGGCTACTGGCATAGGTAGTACAGCAAACAAAACAGTATTAGT    1401
 A  T  L  T  M  P  A  Y  I  D  P  E  N  V  K  K  T  G  N  V  T  L  A  T  G  I  G  S  T  T  A  N  K  T  V  L  V    367

AGATTATGAAAAATATGGTAAGTTTTATAACTTATCTATTAAAGGTACAATTGACCAAATTGATCAAATAATACGTATCGTCAGACAATTATGTCAATCCAAGTG    1511
 D  Y  E  K  Y  G  K  F  Y  N  L  S  I  K  G  T  I  D  Q  I  D  K  T  N  N  T  Y  R  Q  T  I  Y  V  N  P  S  G    404

GAGATAACGTTATTGCGCCGGTTTTAACAGGTAATTAAAACCAAATAACGGATAATGCATTAATAGATCAGCAAAATAACAAGTATTAAAGTATATAAAGTAGATAAT    1621
 D  N  V  I  A  P  V  L  T  G  N  L  K  P  N  T  D  S  N  A  L  I  D  Q  Q  N  T  S  I  K  V  Y  K  V  D  N    440

GCAGCTGATTATCTGAAAGTTACTTTGTGAATCCAGAAAACTTTGAGGATGTCACTAATAGTGTGAATATTACATTCCCAAATCCAAATCAATATAAGTAGAGTTAA    1731
 A  A  D  L  S  E  S  Y  F  V  N  P  E  N  F  E  D  V  T  N  S  V  N  I  T  F  F  P  N  Q  Y  K  V  E  F  N    477

TACGCCTGATGATCAAATTACAACACCGTATATAGTTGTTGTAAATGGTCATATATTGACCCGAATAGCAAAGGTGATTTAGCTTTACGTTCAACTTTATATGGTATAACT    1841
 T  P  D  D  Q  I  T  T  P  Y  I  V  V  V  N  G  H  I  D  P  N  S  K  G  D  L  A  L  R  S  T  L  Y  G  Y  N  S    514

CGAATATAATTGGCCTCTATGTCATGGGACAACGAAGTAGCATTTAATAACGGATTCAGTTCTGGTGTTCTCGACGGGATCCAGATAAACCAGTTGATAATCAGATGAG    1951
 N  I  I  W  R  S  M  S  W  D  N  E  V  A  F  N  N  G  S  G  G  D  G  I  D  K  P  V  V  P  E  Q  P  D  E    550

CCTGGTGAAATTGAACCAATTCCAGAGGATTCTGACCCAGTTCAGATTCGGCAGGATTCAATTCAGATAGCGGTTCAGATTCGGGTTCAGATTCGGGTAGTGATTCTACATC    2061
 P  G  E  I  E  P  I  P  E  D  S  D  P  G  S  D  P  G  S  G  S  G  D  S  N  S  D  S  G  S  D  S  G  S  D  S  T  S    587
                       R →
```

*FIG. 2A-2*

```
AGATAGTGGTTCAGATTCAGCGAGTGATTCAGACTCAGCAAGCGATTCCGACTCAGCGAGCGATTCCGACTCAG    2171
 D  S  G  S  D  S  A  S  D  S  D  S  A  S  D  S  D  S  A  S  D  S  D  S  D    624
ACAATGACTCGGATTCAGATAGCGATTCCGACTCAGACAGTGACTCAGATTCGACTCAGACAGTGACTCAGATTCAGAT  2281
 N  D  S  D  S  D  S  D  S  D  S  D  S  D  S  D  S  D  S  D  S  D  S  D      660
AGCGGATTCAGATTCAGATAGCGATTCAGATTCCGACTCAGACAGCGATTCTGACTCCGACAGTGATTCGACACAGAGCAG  2391
 S  D  S  D  S  D  S  D  S  D  S  D  S  D  S  D  S  D  S  D  S  D  S  D      697
TGATTCCGACTCAGATAGCGATTCCGATTCCGACTCAGATTCAGAGATCAGCGATTCAGATAGCGATTCAGATTCCGACAGTG  2501
 D  S  D  S  D  S  D  S  D  S  D  S  D  S  D  S  D  S  D  S  D  S  D  S  D    734
ACTCAGATTCCGACAGTGACTCGGATTCAGATTCCGACGATTCAGATTCCGACTCAGACTGACTCAGACAGTCATTCGGATTCAGCGAGTGAT   2611
 D  S  D  S  D  S  D  S  D  S  D  S  D  S  D  S  D  S  D  S  D  S  A  S  D    770
TCGGATTCAGATAGTGATTCCGACTCCGACTCGGATTCAGATAGCGATTCGGACTCAGATAGCGATTCAGATTCCGACAGATTC   2721
 S  D  S  D  S  D  S  D  S  D  S  D  S  D  S  D  S  D  S  D  S  D  S  D      807
AGAATCAGACAGCGATTCAGAATCAGACAGCGATTCAGATTCAGACAGTGACTCGGATTCAGATAGTGACTCGGATTCAGACTCAG    2831
 E  S  D  S  D  S  E  S  D  S  D  S  D  S  D  S  D  S  D  S  D  S  A  S  D    844
                                                                            W
GTAGTGACTCCGATTCATCAAGTGATTCCGACTCAGAAAGTGATTCAAATAGCGATTCAGTTCTAACAATAATGTAGTTCCGCCTAATTCACCTAAAAATGGT  2941
 S  D  S  S  S  D  S  D  S  E  S  D  S  N  S  D  S  E  S  S  G  S  N  N  N  V  V  P  P  N  S  S  P  K  N  G    880
                                                                                         M
```

*FIG. 2A-3*

```
ACTAATGCTTCTAATAAAAATGAGGCTAAAGATAGTAAAGAACCATTACCAGATACAGGTTCTGAGATGAAGCAAATACGTCACTAATTTGGGATTATTACCATCAAT    3051
 T  N  A  S  N  K  N  E  A  K  D  S  K  E  P  L  P  D  T  G  S  E  D  E  A  N  T  S  L  I  W  G  L  L  A  S  I     917

AGGTTCATTACTACTTTTCAGAGAAAAAAGAAGAAAATAAGAAGTAATAAGAAATAAGTAATATTAAATTAATCATATGATTCATGAAGAAGCCACCTTAAAAGGTGCT    3161
 G  S  L  L  L  F  R  R  K  K  E  N  K  D  K  K  >                                                                 933

TCTTTTACTTGGATTTTCCAAATATATTGTTTGAATATAATTAATTAATTCATCAACAGTTAATTATTTTAAAAAGGTAGATGTTATATAATTGGCTGGCCGAAAA    3271

AATAGGGTGTAAGGTAGGTTGTTAATTAGGGAAATAAAAATTAAGGAGAAAAATACAGTTGAAAATAAAATTGCTAGTTTTATCATTGGGAGCATTATGTGTATCACAAATTTGGG    3381

AAAGTAATCGTGCGAGTGCAGTGGTTTCTGGGGAGAAGAAATCCATATGTATCTGAGTCGTTGAAACTGACTAATAATAAAAAATAAAATCTAGAACAGTAGAACAGTATAAG    3491
 HindIII
AAAAGCTT                                                                                                           3499
```

FIG. 2A-4

| | BINDS FG | INHIBITS CLUMPING | INHIBIT ADHERENCE | BLOCKS AB | RESIDUES | NUMBER OF RESIDUES |
|---|---|---|---|---|---|---|
| pCF24 | ++ | ++ | ++ | ++ | 23-550 | 527 |
| pCF25 | – | – | – | – | 546-933 | 387 |
| pCF27 | – | – | – | – | 420-550 | 130 |
| pCF28 | – | – | – | +– | 23-424 | 401 |
| pCF29 | – | – | – | – | 23-308 | 285 |
| pCF30 | – | – | ++ | ++ | 332-550 | 218 |
| pCF31 | ++ | ++ | ++ | ++ | 221-550 | 329 |

FIG. 5

S. AUREUS FIBRINOGEN BINDING PROTEIN GENE

This is a Divisional of application No. 09/421,868, filed Oct. 19, 1999, now U.S. Pat. No. 6,177,084, which was a divisional application of application No. 08/293,728, filed Aug. 22, 1994, now U.S. Pat. No. 6,008,341.

FIELD OF THE INVENTION

The invention relates to the isolation of the fibrinogen binding protein gene from *Staphylococcus aureus* and to the use of the fibrinogen binding protein and antibodies generated against it for wound healing, blocking adherence to indwelling medical devices, immunisation or diagnosis of infection.

BACKGROUND OF THE INVENTION

In hospitalised patents *Staphylococcus aureus* is an important cause of infections associated with indwelling medical devices such as catheters and prostheses (Maki, 1982; Kristinsson, 1989) and non-device related infections of surgical wounds. A recent significant increase in isolates from European and US hospitals which are resistant to several antibiotics and the potential threat of emergence of vancomycin resistance in *S. aureus* has reinforced the importance of developing alternative prophylactic or vaccine strategies to decrease the risk of nosocomial infections due to *S. aureus*.

Initial localised infections can lead to more serious invasive infections such as septicaemia and endocarditis. In infections associated with medical devices, plastic and metal surfaces become coated with host plasma and matrix proteins such as fibrinogen and fibronectin shortly after implantation (Baier, 1977; Kochwa et al, 1977; Cottonaro et al, 1981). The ability of *S. aureus* to adhere to these proteins is believed to be a crucial determinant for initiating infection (Vaudaux et al, 1989, 1993). Vascular grafts, intravenous catheters, artificial heart valves and cardiac assist devices are thrombogenic and are prone to bacterial colonization. *S. aureus* is the most damaging pathogen of such infections.

Fibrin is the major component of blood clots and fibrinogen/fibrin is one of the major plasma proteins deposited on implanted biomaterial. There is considerable evidence that bacterial adherence to fibrinogen/fibrin is of importance in initiation of device related infection. (i) *S. aureus* adheres to plastic coverslips coated in vitro with fibrinogen in a dose-dependent manner (Vaudaux et al, 1989) and to catheters coated in vitro with fibrinogen (Cheung and Fischetti, 1990). (ii) The organism binds avidly via a fibrinogen bridge to platelets adhering to surfaces in a model that mimics a blood clot or damage to a heart valve (Herrmann et al., 1993). (iii) *S. aureus* can adhere to cultured endothelial cells via fibrinogen deposited from plasma acting as a bridge (Cheung et al., 1991). This suggests that fibrinogen could have a direct role in promoting invasive endocarditis. (iv) Mutants defective in a global regulatory gene sar have reduced adherence to fibrinogen and have reduced infectivity in a rat endocarditis infection model (Cheung et al., 1994). While this is indicative of a role for adherence to fibrinogen in initiating endocarditis it is by no means conclusive because sar mutants are pleiotropic and could also lack other relevant factors.

A receptor for fibrinogen often called the "clumping factor" is located on the surface of *S. aureus* cells (Hawiger et al., 1978, 1982). The interaction between bacteria and fibrinogen in solution results in instantaneous clumping of bacterial cells. The binding site for clumping factor of fibrinogen is located in the C-terminus of the gamma chain of the dimeric glycoprotein. The affinity for the fibrinogen receptor is very high (Kd $9.6 \times 10^{-9}$ M) and clumping occurs in low concentrations of fibrinogen. It is assumed that clumping factor also promotes bacterial adhesion to solid-phase fibrinogen and to fibrin.

Clumping factor has eluded previous attempts at molecular characterisation. Reports of attempts to purify clumping factor described molecules with molecular masses ranging from 14.3 kDa to 420 kDa (Duthie, 1954; Switalski, 1976; Davison and Sanford, 1982; Espersen et al., 1985; Usui, 1986; Chhatwal et al., 1987; Lantz et al., 1990) but none were followed up with more detailed analysis. Fibrinogen is often heavily contaminated with IgG and fibronectin and unless specific steps were taken to eliminate them these studies must be suspect.

More recently it has been shown that *S. aureus* releases several proteins that can bind to fibrinogen (Boden and Flock, 1989, 1992, 1994; Homonylo McGavin et al., 1993). One of these is probably the same as the broad spectrum ligand binding protein identified by Homonylo McGavin et al., (1993). Another is coagulase (Boden and Flock, 1989), a predominately extracellular protein that activates the plasma clotting activity of prothrombin. Coagulase binds prothrombin at its N-terminus and also interacts with fibrinogen at its C-terminus (McDevitt et al., 1992). However, a hypothesis that the cell-bound form of coagulase is the clumping factor was disproved when coagulase-defective mutants were shown to retain clumping factor activity (McDevitt et al., 1992). There is no evidence that the fibrinogen binding region of any of these proteins is exposed on the bacterial cell surface and consequently there is no evidence that any is clumping factor.

OBJECT OF THE INVENTION

An object of the present invention is to obtain a minimal fibrinogen binding protein. A further objective is to obtain said protein by means of a genetic engineering technique by using e.g. a plasmid comprising a nucleotide sequence coding for said protein. A further objective is to obtain said protein by chemical synthesis. An additional objective is to generate antisera against said protein.

SUMMARY OF THE INVENTION

The present invention relates to an isolated fibrinogen binding protein gene from *S. aureus*, particularly the DNA molecule having the sequence shown in FIG. 2 and Sequence ID No. 1, or a substantially similar sequence also encoding *S. aureus* fibrinogen binding protein.

The invention also relates to hybrid DNA molecules, e.g. plasmids comprising a nucleotide sequence coding for said protein. Further the invention relates to transformed host micro-organisms comprising said molecules and their use in producing said protein. The invention also provides antisera raised against the above fibrinogen binding protein and vaccines or other pharmaceutical compositions comprising the *S. aureus* fibrinogen binding protein. Furthermore the invention provides diagnostic kits comprising a DNA molecule as defined above, the *S. aureus* fibrinogen binding protein and antisera raised against it.

By "substantially similar" is meant a DNA sequence which by virtue of the degeneracy of the genetic code is not identical with that shown in FIG. 2 and Sequence ID No. 1, but still encodes the same amino-acid sequence; or a DNA sequence and Sequence ID No. 1 which encodes a different amino-acid sequence which retains fibrinogen binding protein activity either because one amino-acid is replaced with another similar amino-acid or because the change (whether it be substitution, deletion or insertion) does not affect the active site of the protein.

DRAWINGS

The invention will be described further with reference to the drawings in which there is shown:

FIG. 1. Adherence of *S. aureus* Newman strains to fibrinogen-coated PMMA coverslips. The number of adherent bacteria is shown as a function of fibrinogen adsorbed on the coverslip. The symbol for Newman wild type is IIIIXIII. Symbols for Newman mutant strains are as follows: mutant 1, -□-; mutant 2, -Δ-; mutant 3, -◇-; mutant 4, -∇-. Symbols for Newman mutants carrying pCF16 are as follows: mutant 1, -■-; mutant 2, -▲-; mutant 3, -◆-; mutant 4-▼-.: The number of bacterial cells bound is shown as CFU (mean +/– range, n=2). In points where range bars are not visible, the bars are smaller than the symbols.

FIG. 2. (A) Nucleotide and deduced amino acid sequence of the clfA gene of *Staphylococcus aureus* strain Newman. The sequence has been lodged in the EMBL Data Library under the accession number Z18852 SAUCF. Putative –35, –10, ribosome binding site (RBS) and transcriptional stop regions are indicated on the nucleotide sequence. For the ClfA protein, the start of the signal peptide (S), non repeat region (A), repeat region (R), wall-spanning region (w) and membrane spanning region (M) are indicated by horizontal arrows. The LPXTG motif is underlined.

(B) Schematic diagram showing the domain organization of the ClfA protein. S, signal peptide; A, non-repeat region; R, repeat region; W, wall region;, M, membrane spanning region and +, positively charged residues. The position of the LPXTG motif is indicated.

Figure 3:
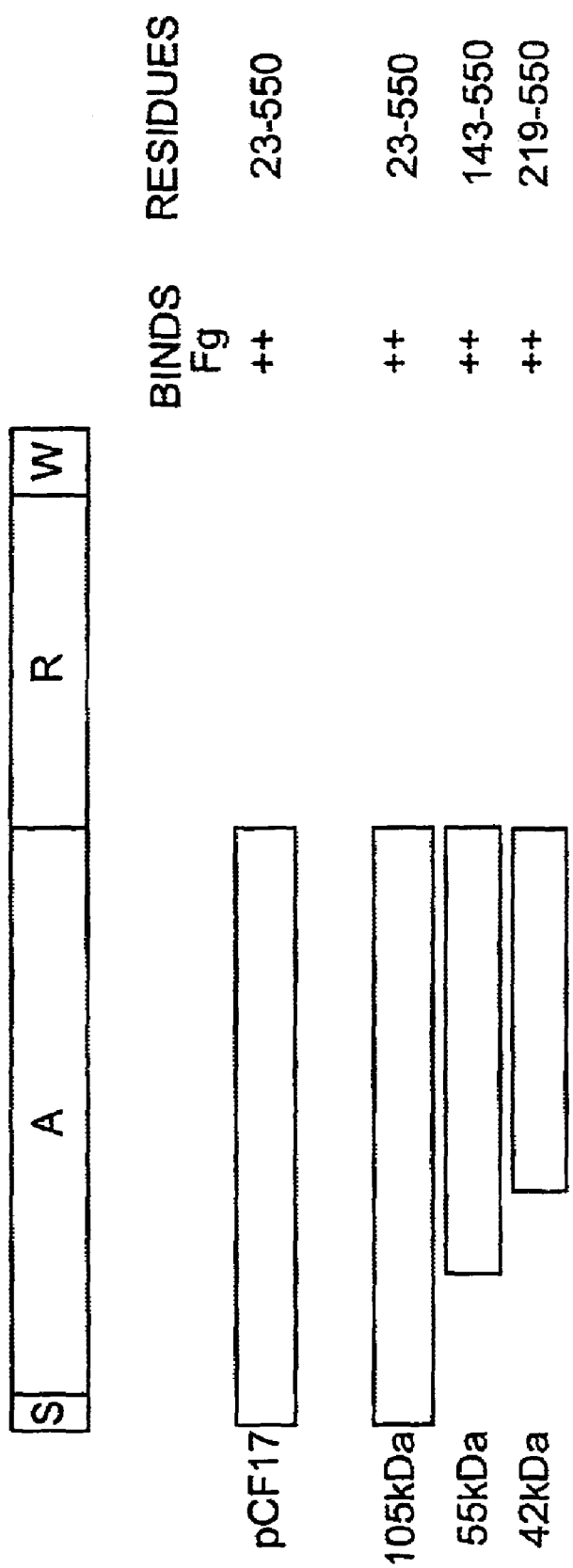

FIG. 3. Proteins purified from *E. coli* TB1 expressing pCF17. A DNA fragment corresponding to the N-terminal half of ClfA (residues 23–550; Region A) was generated by PCR and cloned in-frame into the expression vector pKK233-2 to generate pCF17. The N-terminal sequence was deduced for the three fibrinogen binding proteins (105 kDa, 55 kDa and 42 kDa) purified from an induced culture of *E. coli* carrying pCF17 (Table 1) and the location of each with respect to the A domain and amino acids represented are indicated. Recombinant proteins which possess fibrinogen binding activity are denoted by ++.

Figure 4:
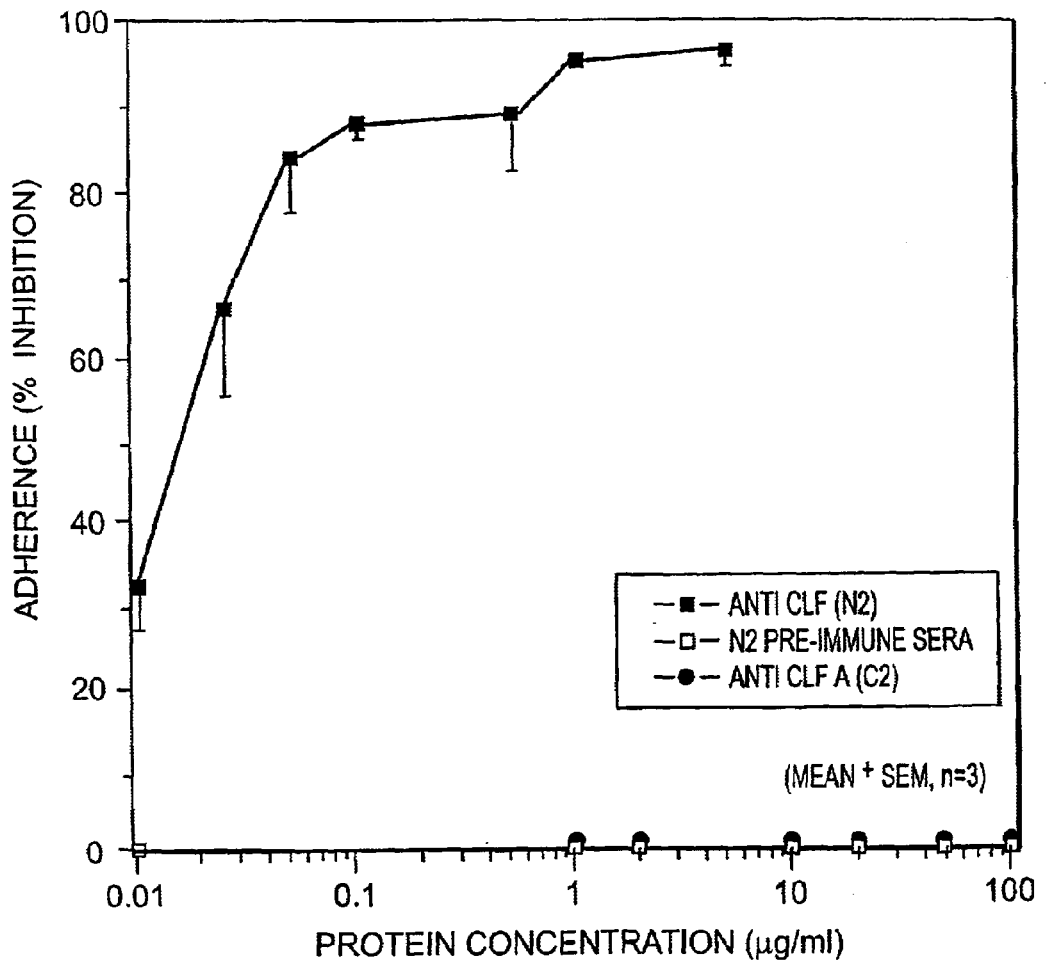

FIG. 4. Inhibition of adherence of strain Newman Δ spa to fibrinogen-coated PMMA coverslips by anti-ClfA sera and pre immune sera. The symbol for anti Region A serum N2 is -■- and the symbol for pre immune serum N2 is -□-. The symbol for anti Region RWM serum C2 is -●-. The percentage inhibition is shown as mean +/– range, n=2. In points where range bars are not visible, the bars are smaller than the symbols.

FIG. 5. Localization of the fibrinogen binding domain of ClfA. DNA fragments corresponding to the different segments of clfA were generated by PCR and cloned in-frame into the fusion protein expression vector pGEX-KG. ClfA truncates were expressed as fusion proteins with glutathione S-transferase. The location of the clfA gene fragments, the amino acids represented and the length of the protein amplified are also indicated. The properties of the recombinant proteins are indicated. Proteins were assessed for (a) ability to bind to fibrinogen in the affinity blotting assay (binds fg), (b) the ability of lysates to inhibit the clumping of bacteria in soluble fibrinogen (inhibits clumping), (c) the ability of lysates to inhibit the adherence of bacteria to solid-phase fibrinogen (inhibit adherence), and (d) the ability of lysates to block neutralising antibodies (blocks Abs). ++, positive reaction; –, negative; ND, not done.

Figure 6B:
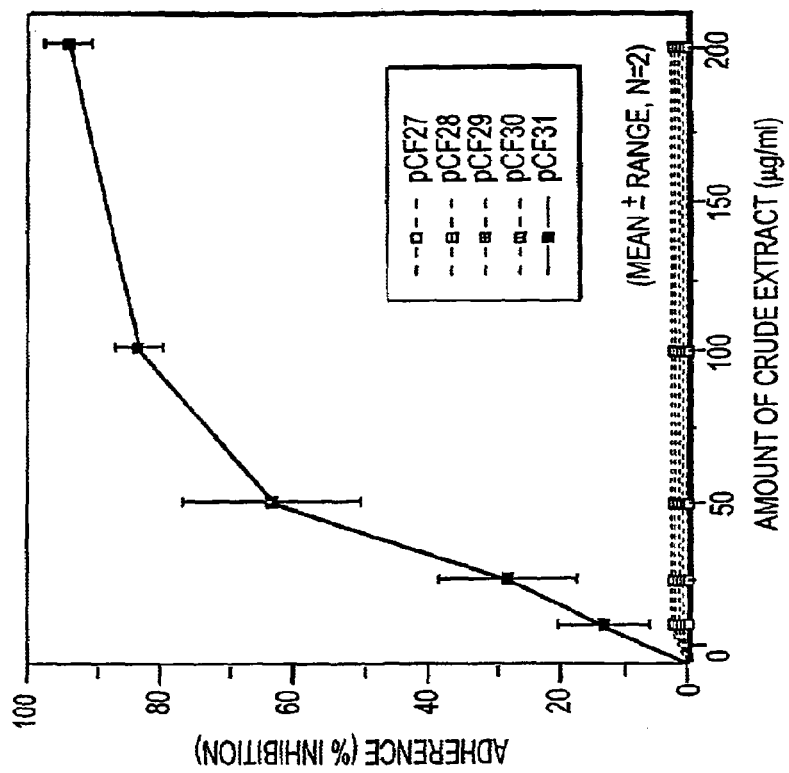
Figure 6A:
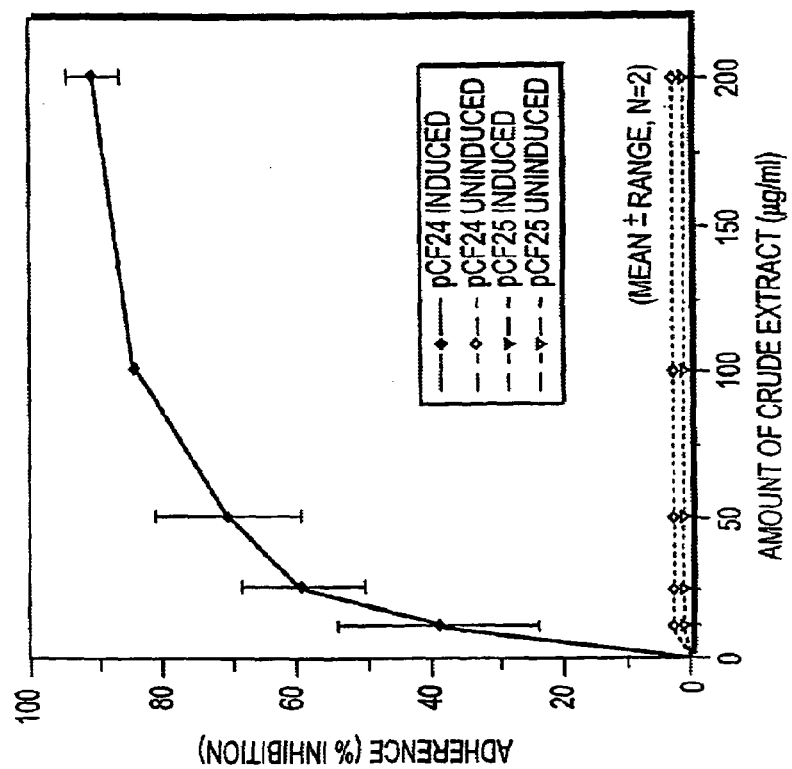

FIG. 6. (A) Inhibition of adherence of *S. aureus* Newman to fibrinogen-coated coverslips by lysates containing ClfA truncates. Symbols are *E. coli* pCF24 uninduced lysate -Δ-, *E. coli* pCF24 induced lysate -▲- *E. coli* pCF25 uninduced lysate -□-, *E. coli* pCF25 induced lysate -■-. The percentage inhibition is shown as mean +/– range, n=2. In points where range bars are not visible, the bars are smaller than the symbols.

(B) Inhibition of adherence of *S. aureus* Newman to fibrinogen-coated coverslips by lysates containing ClfA truncates. Symbols are *E. coli* pCF27 lysate -■-, *E. coli* pCF28 lysate-●-, *E. coli* pCF29 lysate -▲-, *E. coli* pCF30 lysate -▼-, *E. coli* pCF31 lysate -◆-. The percentage inhibition is shown as mean +/– range, n=2. In points where range bars are not visible, the bars are smaller than the symbols.

Figure 7:
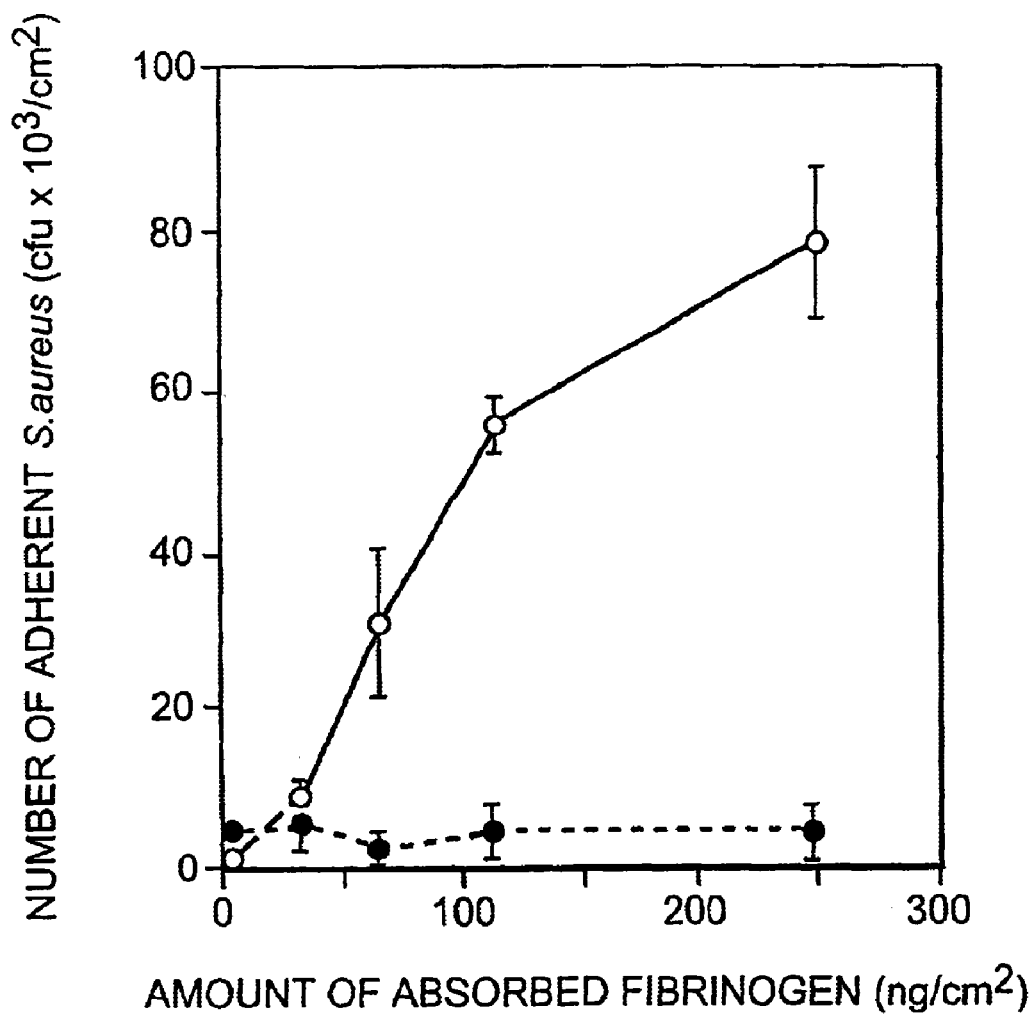

FIG. 7. Adherence of *S. aureus* Newman strains to PMMA coverslips coated in vitro with fibrinogen. The number of adherent bacteria is shown as a function of fibrinogen adsorbed on the coverslip. The symbols are, Newman wild type, -○-; Newman clfA::Tn917, -●-. The number of bacterial cells bound is shown as c.f.u. (mean +/– range, n=2). In points where range bars are not visible, the bars are smaller than the symbols.

Figure 8B:
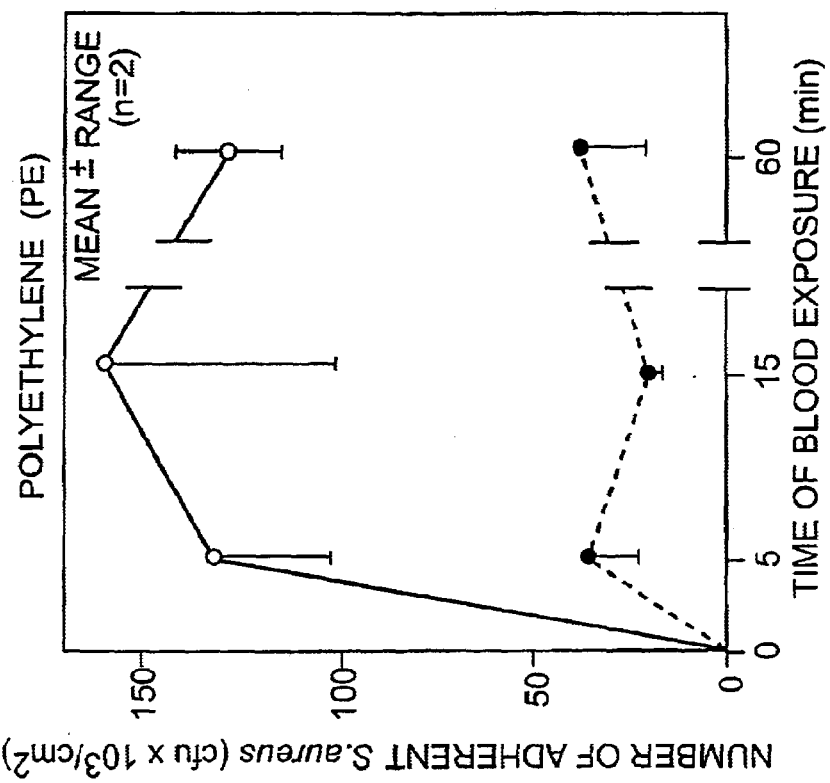
Figure 8A:
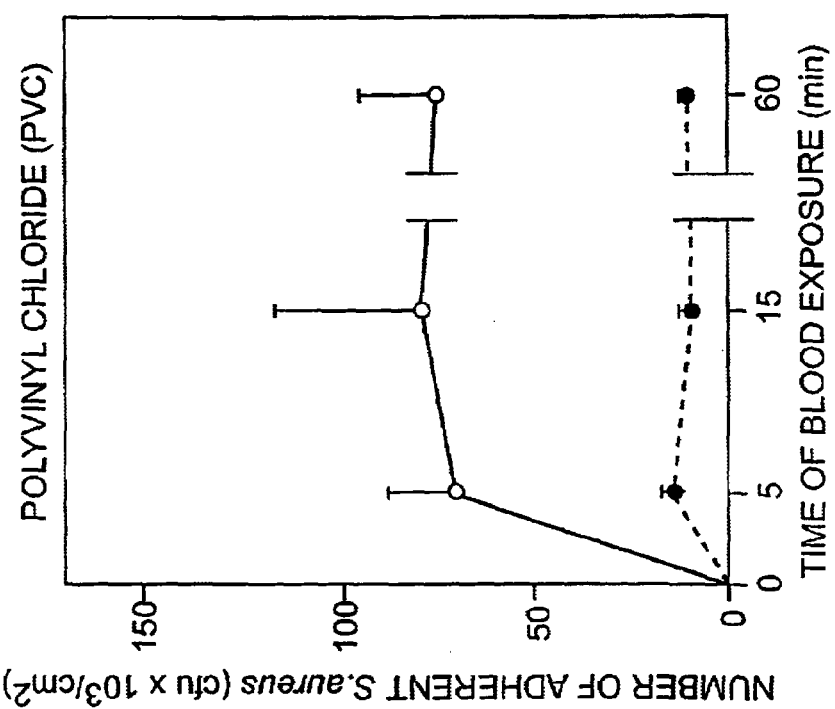

FIGS. 8A–B. Adherence of *S. aureus* Newman strains onto segments of ex vivo polymer tubing exposed to canine blood. Adherence was tested to both ex vivo polyvinylchloride (PVC) and to ex vivo polyethylene (PE). The symbols are, Newman wild type, -○-; Newman clfA::Tn917, -●-. The number of bacterial cells bound is shown as c.f.u. (mean +/– range, n=2). In points where range bars are not visible, the bars are smaller than the symbols.

Figure 9B:
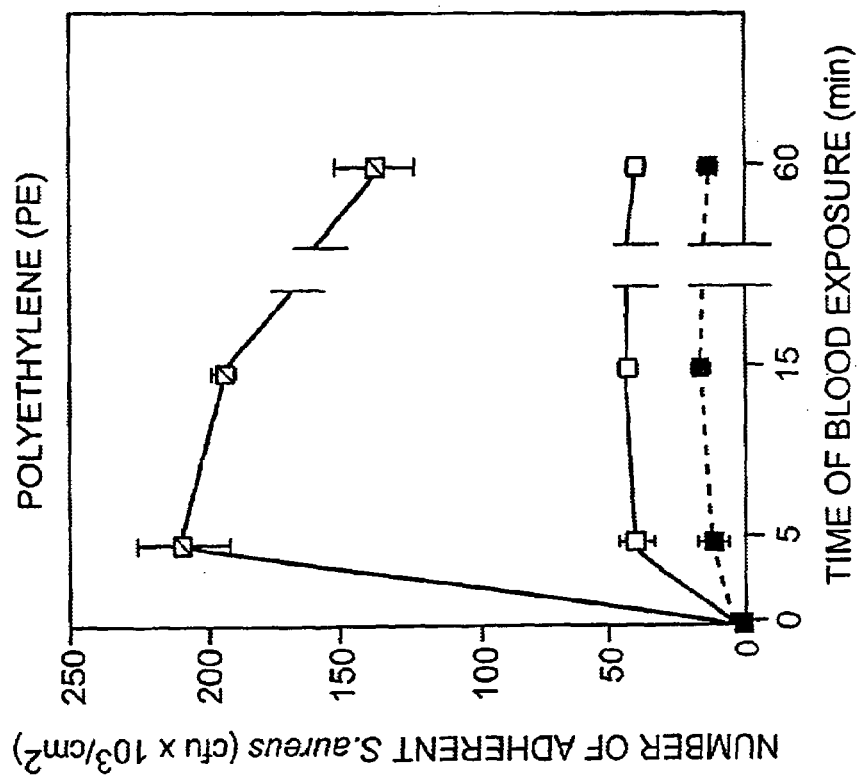
Figure 9A:
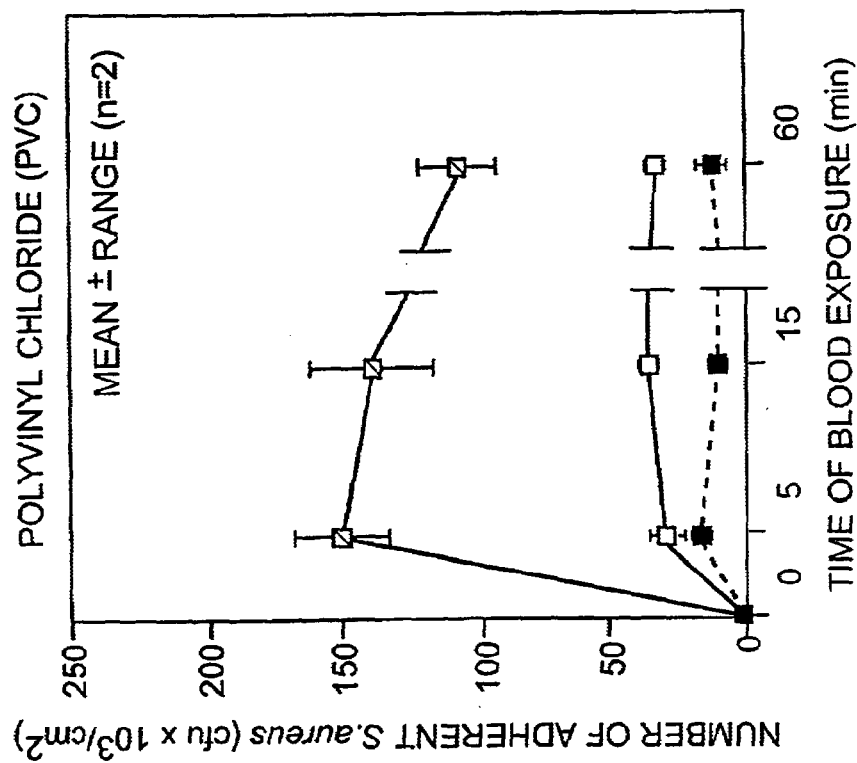

FIGS. 9A–B. Adherence of *S. aureus* 8325-4 strains onto segments of ex vivo polymer tubing exposed to canine blood. Adherence was tested to both ex vivo polyvinylchloride (PVC) and to ex vivo polyethylene (PE). The symbols are: 8325-4 wild type, -□-; 83254 clfA::Tn917, -■-; 8325-4 clfA::Tn917 (pCF4), -⊠-. The number of bacterial cells bound is shown as c.f.u. (mean =/– range, n=2). In points where range bars are not visible, the bars are smaller than the symbols.

CLONING AND SEQUENCING THE CLUMPING FACTOR GENE

In view of the difficulties mentioned above with (i) obtaining pure fibrinogen, (ii) the discrepancies in reported molecular weight of "clumping factor" and (iii) the diversity of different fibrinogen binding proteins, a different approach was taken to identify the clumping factor gene involving isolating insertion mutants that inactivated the clumping phenotype. This has been described in detail by McDevitt et al., (1994).

Transposon Tn917 (Tomich et al., 1980) was used to generate insertion mutants that eliminated the fibrinogen clumping phenotype of *S. aureus* strain Newman. The temperature sensitive plasmid pTV1ts which carries Tn917 (Youngman, 1985) was transferred into strain Newman and several transposon insertion banks were isolated by growing cultures at 43° in broth containing erythromycin (to select for Tn917 after plasmid elimination). Cultures of the banks were mixed with fibrinogen, the agglutinated cells were removed and the surviving cells in the supernatants were screened for clumping factor-deficient mutants. Four mutants were isolated from separate banks. The Tn917 elements were transduced into a wild-type Newman host with phage 85. In each case all the transductants screened had inherited the clumping factor deficiency proving that the Tn917 insertions caused the mutant phenotypes. The clumping factor mutants expressed the same level of coagulase as the wild-type strain, further supporting the conclusion that clumping factor and coagulase are distinct entities.

The mutants were analyzed by Southern hybridization using an internal fragment of Tn917 as a probe in order to identify HindIII junction fragments comprising transposon and flanking chromosomal sequences. A junction fragment from one mutant was cloned using standard techniques in plasmid vector pUC18 (Yanisch Perron et al., 1985). A fragment comprising only chromosomal DNA flanking the transposon was isolated from this plasmid and used in turn as a probe in a Southern blot of genomic DNA of Newman wild-type and each of the mutants. A HindIII fragment of 7 kb that hybridized in Newman wild-type was missing in each of the mutants. Genomic DNA of Newman wild-type was cleaved with HindIII and ligated with plasmid pUC18 cut with the same enzyme and transformed into E. coli TBI (Yanisch-Perron et al., 1985). Transformants were screened by colony hybridisation using the junction fragment probe. Plasmid pCF3 (pUC18 carrying the 7 kb HindIII fragment) was isolated. Plasmid pCF3 was deposited at the NCIMB, Amberdeen, Scotland on Jul. 2, 1998 under the Accession No. NCIMB40959, such deposit complying with the terms of the Budapest Treaty.

The 7 kb HindIII fragment was subcloned into pCL84, a single copy non-replicating vector which integrates into the chromosome of S. aureus (Lee et al., 1991), forming pCF16. pCF16 was transformed into S. aureus strain CYL316 (Lee et al., 1991) selecting for tetracycline resistance. The integrated plasmid was then transduced with phage 85 into each of the Newman clf mutants. In a microtitre clumping assay the Newman mutants were completely devoid of activity even at the highest concentrations of fibrinogen, whereas the wild-type had a titre of 2048 and could interact productively with very low concentrations of fibrinogen. The integrated single copy plasmid pCF16 restored the clumping activity of each of the mutants to the same level as that of the parental strain. Thus the HindIII fragment must express a functional protein which complements the clumping deficiency of the mutants.

S. aureus Newman adhered to solid-phase fibrinogen coated onto polymethylmethacrylate (PMMA) coverslips in a concentration dependent manner (FIG. 1). Each clf mutant showed drastic reduction in adherence. This was restored to the level of the parental strain by pCF16. This data shows that the ability of Newman to form clumps in soluble fibrinogen correlates with bacterial adherence to solid-phase fibrinogen.

Figure 2B:
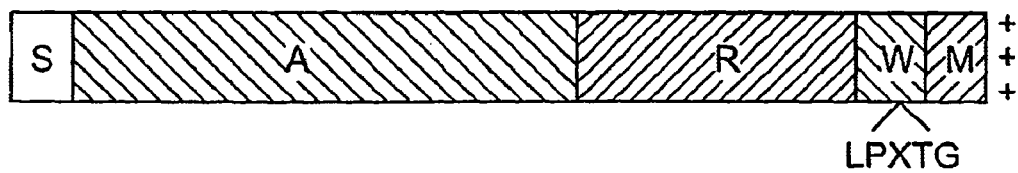

Fragments from the 7 kb HindIII fragment in pCF3 were subcloned into pGEM7 Zf (+) (Promega). The smallest fragment which still expressed the fibrinogen binding activity was a 3.5 kb HindIII-KpnI fragment which is contained in the plasmid pCF10 which was deposited at the National Collections of Industrial and Marine Bacteria, Ltd., Aberdeen, Scotland, in September, 1994, and which was accorded Accession No. 40674. The DNA sequence of this fragment was obtained using standard techniques and has been lodged in the EMBL Data Library under the accession number Z18852 SAUCF. A single open reading frame of 2799 bp was identified (FIG. 2A) and Sequence ID No. 1. The orf is called clfA and the gene product the ClfA protein. The predicted protein is composed of 933 amino acids (molecular weight 97,058 Da see Sequence ID Nos. 1 and 2). A putative signal sequence of 39 residues was predicted. The predicted molecular weight of the mature protein is 92 kDa. Following the signal sequence is a region of 520 residues (Region A) which precedes a 308 residue region (region R) comprising 154 repeats of the dipeptide serine-aspartate (FIGS. 2A and 2B Sequence ID No. 2). The C terminus of ClfA has features present in surface proteins of other Gram positive bacteria (Schneewind et al., 1993) that are responsible for anchoring the protein to the cell wall and membrane: (i) residues at the extreme C-terminus that are predominantly positively charged, (ii) a hydrophobic region which probably spans the cytoplasmic membrane and (iii) the sequence LPDTG which is homologous to the consensus sequence LPXTG that occurs in all wall-associated proteins of Gram positive bacteria. This strongly suggests that ClfA is a wall-associated protein and that the N terminal part is exposed on the cell surface.

It is not obvious from the primary structure of ClfA or by comparison of ClfA with other ligand binding proteins of S. aureus (fibronectin binding protein, Signas et al., 1989; collagen binding protein, Patti et al., 1992) which part of ClfA interacts with fibrinogen.

Results (1) Purifying the N-terminal Half of the Fibrinogen Receptor (ClfA)

A DNA fragment corresponding to the N-terminal half of ClfA (residues 23–550; Region A) was generated by polymerase chain reaction (PCR) and cloned in-frame into the expression vector pKK233-2 (Amann and Brosius, 1985) to generate pCF17 (FIG. 3). Expression of recombinant Region A was induced by adding isopropyl Beta-D-thiogalactoside (IPTG) to exponential cultures. Induced cultures contained two proteins of 105 kDa and 55 kDa which reacted with fibrinogen in a Western ligand blotting assay. A fibrinogen-Sepharose 4B column was made by the method recommended by the manufacturer (Pharmacia). A sample of an induced culture containing these fibrinogen binding proteins was passed into the fibrinogen Sepharose 4B column. Four proteins were eluted: –105 kDa, 55 kDa, 42 kDa and 75 kDa (trace amounts). In a separate purification experiment, the 42 kDa protein was purified to homogeneity. Only the 105 kDa, 55 kDa and 42 kDa proteins bound to fibrinogen in the Western ligand blotting assay. The N-terminal sequence of these proteins was determined (Table 1). The 75 kDa protein was present in trace amounts (1–2 pmoles) and is not related to ClfA. The three predominant proteins bound to fibrinogen in the Western blotting assay and are related to the region A (see FIG. 3). The 105 kDa protein represents the intact Region A while the 55 kDa and 42 kDa proteins are breakdown products. The apparent molecular weights of the native region A and breakdown products of region A are much higher than that predicted from the DNA sequence (Table 1).

(2) Antibodies to the Region A of the ClfA Protein (Residues 23–550)

A rabbit was immunised with 30 micro 9 of a mixture of the 105 kDa, 75 kDa, 55 kDa and 42 kDa proteins along with Freund's complete adjuvant. The immune sera was called N2. One rabbit was also immunised with 18 micro g of the purified 42 kDa ClfA truncate and the immune serum for this was called N3. Bacterial interaction with fibrinogen can be measured by a quantitative clumping titration assay (Switalski, 1976). In this assay, doubling dilutions of a fibrinogen solution (1 mg/ml) are mixed in a microtitre dish with a suspension of $2 \times 10^7$ cells for 5 min with gentle shaking. A standard clumping concentration of fibrinogen was defined as 2× the titre. To this was added varying amounts of the anti-ClfA serum to measure the minimum inhibitory concentration that stops the clumping reaction (Table 2). Both N2 and N3 sera were potent inhibitors of the clumping of bacteria. Preimmune sera did not inhibit the clumping of bacteria. N2 sera also had a potent inhibitory activity on bacterial adhesion to surface-bound fibrinogen in the coverslip assay (McDevitt et al., 1992, 1994), expressing 95% inhibition at 1 micro g protein/ml (FIG. 4). Preimmune sera did not have any inhibitory activity even at a protein concentration of 100 micro g/ml (FIG. 4). In addition, antisera raised against regions R, W and M (C2) (see section 4 below) failed to inhibit adherence even at 100 micro g/ml (FIG. 4).

(3) Localisation of the Fibrinogen Binding Domain of the ClfA Protein

DNA fragments corresponding to the Region A of ClfA (residues 23–550) and C terminal regions R, W and M (residues 546–933) were generated by PCR (standard conditions,) and cloned in-frame into the fusion protein expression vector pGEX-KG (Guan and Dixon, 1991) to generate pCF24 and pCF25 respectively (see FIG. 5). These ClfA truncates were expressed as fusion proteins with glutathione S-transferase. An induced lysate of E. coli pCF24 (residues 23–550) expressed a fusion protein that bound to fibrinogen in a Western affinity blotting assay with peroxidase labelled fibrinogen (FIG. 5). In addition, this lysate inhibited the clumping of bacteria with soluble fibrinogen in the clumping assay (Table 3 and FIG. 5) and also inhibited the adherence of bacteria to immobilised fibrinogen in the coverslip assay in a dose dependent fashion (FIG. 6). A lysate of E. coli pCF25 (residues 546–933) induced with IPTG expressed a fusion protein that failed to bind to fibrinogen in the Western blotting assay (FIG. 5). In addition, this lysate did not inhibit the clumping of bacteria in the clumping assay (Table 3) and did not inhibit adherence to immobilized fibrinogen in the adherence assay (FIG. 6). Uninduced lysates from both pCF24 and pCF25 failed to inhibit both clumping and adherence (Table 3 and FIG. 6).

A synthetic peptide (SDSDSDSDSDSDGGGC Sequence ID No. 16) designed to mimic the C-terminal repeat region of ClfA failed to inhibit the clumping of bacteria in the clumping assay when up to 107 micro g/ml was tested. In addition, the synthetic peptide failed to inhibit the adherence of bacteria in the adherence assay even at a concentration of 100 micro g/ml. Taken together, this data suggests that the fibrinogen binding domain of ClfA is located in the A domain rather than in the regions R, M, and W. It confirms the data in Table 1 which dealt with purifying fibrinogen binding proteins expressed from pCF17 and also suggests that an N-terminal ClfA protein can act both as a potent inhibitor of cell clumping in fibrinogen and also as a potent inhibitor of the adherence of bacteria to fibrinogen coated surfaces.

The fibrinogen binding domain was further localised within region A. Segments of region A were amplified by PCR and cloned into the pGEX-KG vector. Lysates from IPTG-induced cultures were examined for the presence of fibrinogen binding fusion proteins, for the ability to inhibit the clumping of bacteria in the fibrinogen clumping assay and for the ability to inhibit adherence to immobilised fibrinogen in the adherence assay. The fusion protein of pCF31 (residues 221–550) was the smallest truncate that still expressed a fibrinogen binding activity (FIG. 5). It is almost identical in composition to the purified 42 kDa protein (residues 219–550) described above. The fusion proteins from pCF27, pCF28, pCF29 and pCF30 all failed to bind to fibrinogen in the Western affinity blotting assay, despite reacting with antibodies generated against the A domain of ClfA (FIG. 5). In addition, a lysate containing the fusion protein expressed by pCF31 was the only one to inhibit the fibrinogen clumping reaction (Table 3) and to inhibit the adherence of bacteria to immobilised fibrinogen in the adherence assay (FIG. 6). These results suggest that the fibrinogen binding site is quite extensive or that its correct conformation is determined by flanking sequences.

An antibody neutralisation assay was adopted to help localise further the active site within residues 221–550. This assay was conducted with a protein A negative deletion mutant of S. aureus strain Newman (Patel et al., 1987) to prevent non specific reaction with IgG. Polyclonal antibodies raised against the A region of ClfA (N2) inhibited the clumping of bacteria in soluble fibrinogen (see section 2 above). In the standard clumping assay with the clumping concentration at 2× the titre, the concentration of lysates that blocked the inhibitory activity of 4.68 micro g of serum (2× the inhibitory concentration, Table 2) was determined. The lysates containing ClfA fusion proteins were assayed for their ability to neutralise the inhibiting activity of the antibodies. Truncates containing the active site might be able to adsorb out antibodies generated against the active site and thus neutralise the blocking effect on cell clumping. The lysates containing proteins expressed by pCF24 and pCF31 neutralised the inhibiting activity of the antibodies while a lysate containing the fusion protein expressed by pCF25 (Region R, W and M) did not inhibit (Table 4). Lysates containing small fusion proteins expressed by pCF30 were able to neutralise the inhibiting activity of antibodies while lysates containing fusion proteins expressed by pCF27 and pCF29 had no such activity (Table 4). Taken together this suggested that the active site is located in a 218 residue region between residues 332 and 550.

(4). Antibodies to the C-Terminal Half of the ClfA Protein (Residues 546–933)

The fusion protein present in a lysate of E. coli pCF25 (residues 546–933) induced with IPTG was purified to homogeneity by using glutathione sepharose-affinity chromatography as described by Guan and Dixon, (1991). A rabbit was immunised with 20 micro g of the fusion protein along with Freund's complete adjuvant. The immune sera was called C2. This serum failed to inhibit the clumping of bacteria in the clumping assay (Table 2) and also failed to inhibit bacterial adhesion to surface bound fibrinogen in the coverslip assay even at 100 micro g/ml (FIG. 4).

(5) Identification of the Native Fibrinogen Receptor

Proteins released from the cell wall of S. aureus strains and a lysate of E. coli expressing the cloned clfA gene were studied by Western immunoblotting with anti ClfA antibodies in order to identify ClfA protein(s). A lysate of E. coli TB1 (pCF3) (carrying the cloned clfA gene) contained several immunoreactive proteins. The largest of these was ca. 190 kDa. The smaller proteins are probably derivatives caused by proteolysis. S. aureus strain Newman also expresses a ca. 190 kDa immunoreactive protein. A smaller immunoreactive protein of ca. 130 kDa was also detected and is probably also caused by proteolysis. Despite the presence of protease inhibitors and studying proteins released from cells harvested at different stages in the growth cycle (from mid-exponential to late stationary), two proteins of these sizes were always present (data not shown). Both proteins were absent in extracts of the clumping factor negative transposon insertion mutant of Newman indicating that they are products of the clfA gene.

Previously we reported the size of the ClfA protein to be ca. 13 kDa (McDevitt et al., 1994) in an affinity blotting assay with fibrinogen and peroxidase labelled anti-fibrinogen antibodies. Our current immunoblotting assay is much more sensitive than the affinity blotting assay. In addition, we now know that the ClfA protein is very sensitive to degradation. Indeed the predominant immunoreactive protein detected in samples from both *E. coli* TB1 (pCF3) and *S. aureus* strain Newman which have been frozen and thawed more than twice is 130 kDa indicating that the ca. 190 kDa protein is labile (data not shown). Thus, the ca. 130 kDa protein detected in the affinity blotting assay is most probably a smaller derivative of ClfA. The apparent size of the native ClfA protein of strain Newman appears to be ca. 190 kDa. This is double that predicted from the DNA sequence, but this might be due to the unusual structure and is consistent with the aberrantly high apparent molecular weight of recombinant proteins (Table 1). The recombinant N-terminal Region A protein expressed by *E. coli* pCF17 also had an unexpectedly high apparent molecular weight.

(6) Surface Localization of the ClfA Protein by Immunofluorescent Microscopy

Anti-ClfA region A sera (N2) was used to confirm that Region A of ClfA is exposed on the bacterial cell surface. Protein A-deficient mutants of Newman and Newman clfA::Tn917 (clumping factor transposon insertion mutant) were isolated by transducing the Δ spa::Tc$^r$ mutation from 8325-4 Δ spa::Tc$^r$ to strains Newman and Newman clfA::Tn917 using phage 85. Protein A-deficient mutants were used to prevent non-specific interaction with rabbit IgG. Cells from overnight cultures of strains Newman Δ spa::Tc$^r$ and Newman Δ spa::Tc$^r$ clfA::Tn917 were diluted to As60=0.6–1.0 and fixed to glass slides using gluteraldehyde. The slides were then incubated in anti-ClfA region A serum (N2, 1 in 200) followed by fluorescein conjugated swine anti-rabbit serum (Dakopatts, 1 in 40). The cells were studied for fluorescence by microscopy (Nowicki et al., 1984). Newman Δ spa::Tc$^r$ cells fluoresced while Newman Δ spa::Tc$^r$ clfA::Tn917 cells did not. This confirmed that region A of ClfA is exposed on the cell surface of wild-type Newman and that this ClfA protein is absent in the clumping factor deficient mutant.

(7) Role of the Fibrinogen Receptor in Adherence to In Vitro- and Ex Vivo-Coated Polymeric Biomaterials A mutant of strain Newman defective in the clumping factor (clfA1::Tn917) and a complemented mutant bearing pCF16 were studied for adherence properties to biomaterials coated in vitro with fibrinogen and to ex vivo biomaterial. A canine arteriovenous shunt has been developed as a model to study plasma protein adsorption onto intravenous catheters from short-term blood-biomaterial exposures and to identify host proteins promoting adhesion of *Staphylococcus aureus* (Vaudaux et al., 1991).

*S. aureus* strain Newman adheres strongly (in a concentration dependent fashion) to polymethylmethacrylate (PMMA) coverslips coated in vitro with canine fibrinogen (FIG. 7). In contrast, the fibrinogen receptor mutant was significantly defective (>95%) in its ability to adhere to the canine fibrinogen coated coverslips (FIG. 7). In the ex vivo model, either polyethylene or polyvinyl chloride tubing was exposed to canine blood for 5, 15 or 60 min at a flow rate of 300 ml/min, then flushed in phosphate buffered saline (PBS), cut into 1.5 cm segments and preincubated in 0.5% albumin in PBS to prevent non-specific staphylococcal attachment. Then, each segment was incubated with 4×10$^6$ CFU/ml of [3H]thymidine-labelled *S. aureus* for 60 min at 37° C. in an in vitro adherence assay. When compared with the wild-type strain Newman, the fibrinogen receptor mutant strain showed a strong decrease (>80%) in attachment to ex vivo polyvinyl chloride and polyethylene tubings (FIGS. 8A–B). In addition, strain 8325-4 (which binds poorly to fibrinogen-coated coverslips in vitro and to the ex vivo polymer tubings) showed a significant increase in its ability to adhere to the two different ex vivo polymer tubings when complemented with a plasmid (pCF4) expressing the fibrinogen receptor gene (FIG. 9A–B).

The data shows that fibrinogen is the major plasma protein in a short-term blood material interaction to promote staphylococcal adherence and the possession of the fibrinogen receptor is a major determinant in the ability of *S. aureus* to adhere to ex vivo biomaterials.

(8) Role of the Fibrinogen Receptor in the Pathogenesis of Experimental Endocarditis

*S. aureus* strain Newman, the fibrinogen receptor mutant strain of Newman (clfA::Tn917) and a fibrinogen receptor mutant complemented with the clfA+ integrating plasmid pCF16 were compared in a previously described model of experimental endocarditis (Garrison and Freedman, 1970). This rat model investigates the early events in experimental endocarditis with catheter-induced aortic vegetations (Veg). Groups of >/–8 rats were challenged with an inoculum that resulted in 90% of vegetations being colonised by the wild-type organism (ID90). Animals were injected intravenously with the same inocula of Newman clfA and Newman clfA (pCF16). Animals were killed 12 hours after inoculation and quantitative cultures of the blood, spleen and Veg were performed. Table 5 shows the percentage of rats infected.

The data show that a mutant lacking the fibrinogen receptor was significantly less able to infect the catheter-induced aortic vegetations (decrease of 49%) when compared with the wild type strain Newman. In addition, the complemented strain had restored infectivity. The fact that all three strains infected the spleens with similar numbers suggests that the presence or absence of the fibrinogen receptor interfered specifically with bacterial colonisation of the catheter-induced aortic vegetation.

This model strongly implicates the fibrinogen receptor as an important adhesin in the pathogenesis of *S. aureus* endocarditis and other cardiovascular infections associated with intravenous catheters, artificial heart valves and intravenous shunts.

Uses of the Invention

1. The fibrinogen binding protein or fragment containing the fibrinogen binding region can be used as a vaccine to protect against human and animal infections caused by *S. aureus*. For example, the fibrinogen binding protein or fragment containing the fibrinogen binding region can be used as a vaccine to protect ruminants against mastitis caused by *S. aureus* infections.

2. Polyclonal and monoclonal antibodies raised against the fibrinogen binding protein or a fragment containing the fibrinogen binding domain can be used to immunise passively by intravenous injection against infections caused by *S. aureus*.

3. The fibrinogen binding protein or an active fragment can be administered locally to block *S. aureus* from colonising and infecting a wound.
4. The antibody against the fibrinogen binding protein can be administered locally to prevent infection of a wound.
5. The fibrinogen binding protein or an active fragment or antibodies against the fibrinogen binding protein can be used to block adherence of *S. aureus* to indwelling medical devices such as catheters, replacement heart valves and cardiac assist devices.
6. The fibrinogen binding protein or an active fragment or antibodies against the fibrinogen binding protein can be used in combination with other blocking agents to protect against human and animal infections caused by *S. aureus*.
7. The fibrinogen binding protein can be used to diagnose bacterial infections caused by *S. aureus* strains. The fibrinogen binding protein can be immobilised to latex or Sepharose (Trade Mark), and sera containing antibodies are allowed to react; agglutination is then measured.
8. The fibrinogen binding protein can be used in an ELISA test.
9. DNA gene probe for the fibrinogen binding protein for ELISA tests.
10. Antibodies to the fibrinogen binding protein can be used to diagnose bacterial infections caused by *S. aureus* strains.

TABLE 1

ClfA proteins.

| Protein mol. wt. apparent* | wt. predicted@ | N-terminal sequence | ClfA residues |
|---|---|---|---|
| 105 kDa | 57 kDa | VGTLIGFGLL, Sequence ID No. 17 | 23-32 |
| 15 kDa | ND | GKIIGID, Sequence ID No. 18 | not related |
| 55 kDa | 44 kDa | MNQTSNETTFNDTNTV, Sequence ID No. 19 | 143-157 |
| 42 kDa | 36 kDa | AVAADAPAAGTDITNQLT, Sequence ID No. 20 | 220-237 |
| Native ClfA 190 kDa | 92 kDa | | |

*determined from migration on SDS-PAGE and Western blotting.
@predicted from the amino acid sequence
ND not determined.

TABLE 2

Inhibition of clumping with anti-ClfA sera.

| Sera | Inhibiting concentration* (micro g) |
|---|---|
| N2 | 2.34 |
| N3 | 2.34 |
| Preimmune N2 | >300.00 |
| Preimmune N3 | >300.00 |
| C2 | >300.00 |

*Average of 3 experiments.

TABLE 3

Inhibition of clumping with lysates containing truncated ClfA proteins.

| Lysate | Inhibiting concentration* (micro g) |
|---|---|
| pCF24 | 9.37 |
| pCF25 | >300.00 |

TABLE 3-continued

Inhibition of clumping with lysates containing truncated ClfA proteins.

| Lysate | Inhibiting concentration* (micro g) |
|---|---|
| pCF24 Uninduced | >300.00 |
| pCF25 Uninduced | >300.00 |
| pCF27 | >300.00 |
| pCF28 | >300.00 |
| pCF29 | >300.00 |
| pCF30 | >300.00 |
| pCF31 | 9.37 |

*Average of 3 experiments.

TABLE 4

The ability of lysates to block the inhibiting effect of anti-ClfA N2 sera on cell clumping.

| Lysate | Blocking concentration* (micro g) |
|---|---|
| pCF24 | 1.17 |
| pCF25 | >75.00 |
| pCF27 | >75.00 |
| pCF28 | >75.00 |
| pCF29 | >75.00 |
| pCF30 | 2.34 |
| pCF31 | 2.34 |

*Average of 3 experiments.

TABLE 5

Experimental endocarditis

| % infected | Newman | Newman clfA::Tn917 | Newman clfA::Tn917 pCFl6 clfA+ |
|---|---|---|---|
| vegetation | 84% | 43%* | 83% |
| blood cultures | 70% | 30%* | 50% |
| spleen (× log CFU/g) | 3.16 | 3.11 | 3.59 |

*p = 0.05 when compared to other groups

REFERENCES

Amann, E. and Brosius, J. (1985). 'ATG Vectors' for regulated high-level expression of cloned genes in *Escherichia coli*. Gene 40, 183–190.

Baier, R. E. (1977). The organisation of blood components near interfaces. Ann N. Y. Acad Sci 283:17–36.

Boden, M. K., and Flock, J. I. (1989). Fibrinogen-binding protein/clumping factor from *Staphylococcus aureus*. Infect. Immun. 57: 2358–2363.

Boden, M. K., and Flock, J. I. (1992). Evidence for three different fibrinogen binding proteins with unique properties from *Staphylococcus aureus* strain Newman. Microbiol. Pathogen., 12(4), 289–298.

Boden, M. K., and Flock, J. I. (1994). Cloning and characterization of a gene for a 19 kDa Fibrinogen-binding protein from *Staphylococcus aureus*. Molec. Microbiol. 12(4), 599–606.

Chhatwal, G. S., Albohn, G. and Blobel, H. (1987). Interaction between fibronectin and purified staphylococcal clumping factor. FEMS Microbiol. Lett. 44, 147–151.

Cheung, A. and Fischetti, V. A. (1990). Role of surface proteins in staphylococcal adherence to catheters in vitro. J. Infect. Dis. 161, 1177–1186.

Cheung, A. L., Kirshnan, N., Jaffe, E. A. and Fischetti, V. A. (1991). Fibrinogen acts as a bridging molecule in the adherence of *Staphylococcus* aureus to cultured human endothelial cells. J. Clin. Invest. 87, 2236–2245.

Cheung, A. L., Yeaman, M. R. Sullam, P. M., Witt, M. D. and Bayer A. S. (1994). Role of the sar locus of *Staphylococcus aureus* in induction of endocarditis in rabbits. Infect. Immun. 62, 1719–1725.

Cottonaro, C. N., Roohk, H. V., Shimica, G., and Sperling, D. R. (1981). Quantitation and characterization of competitive protein binding to polymers. Trans Am. Soc. Artif. Inter. Organs 27:391–395.

Davison, V. E., and Sandford, B. A. (1982). Factors influencing adherence of *Staphylococcus aureus* to Influenza A virus-infected cell cultures. Infect. Immun. 37:946–955.

Duthie, E. S. (1954). Evidence of two forms of staphylococcal coagulase. J. Gen. Microbiol. 10:427–436.

Espersen, F., Clemmensen, I., and Barkholt, V. (1985). Isolation of *Staphylococcus aureus* clumping factor. Infect. Immun. 49:700–708.

Garrison, P. K. and Freedman, L. R. (1970). Experimental endocarditis. 1. Staphylococcal endocarditis in rabbits resulting from placement of a polyethylene catheter in the right side of the heart. Yale J. Biol. Med. 42, 394–410.

Guan, K. and J. E. Dixon. (1991). Eukaryotic proteins expressed in *Escherichia coli*: An improved thrombin cleavage and purification procedure of fusion proteins with glutathione S-transferase. Anal. Biochem. 192, 262–267.

Hawiger, J. S, Hammond, D. K., Timmons, S. and Budzynski, A. Z. (1978). Interaction of human fibrinogen with staphylococci: presence of a binding region on normal and abnormal fibrinogen variants and fibrinogen derivatives. Blood 51:799–812.

Hawiger, J. S., Timmons, S., Strong, D. D., Cottrell, B. A., Riley, M., and Doolittle, R. F. (1982). Identification of a region of human fibrinogen interacting with staphylococcal clumping factor. Biochemistry 21:1407–1413.

Herrmann, M., Lai, Q. J., Albrecht, R. M., Mosher, D. F. and Proctor, R. A. (1993). Adhesion of *Staphylococcus aureus* to surface-bound platelets: role of fibrinogen/fibrin and platelet integrins. J. Infect. Dis. 167, 312–322.

Homonylo McGavin, M., Krajewska-Pietrasik, D., Ryden, C. and Hook, M. (1993). Identification of a *Staphylococcus* aureus extracellular matrix-binding protein with broad specificity. Infect. Immun. 61, 2479–2485.

Kochwa, S., Litwak, R. S. Rosenfield, R. E. and Leonard, E. F. (1977). Blood elements at foreign surfaces: a biochemical approach to study the adsorption of plasma proteins. Ann. NY Acad Sci 238, 27–49.

Kristinsson, K. G. (1989). Adherence of staphylococci to intravascular catheters. J. Med. Microbiol. 28:249–257.

Lantz, M. S., Allen, R. D., Bounelis, P., Switzalski, L. M. and Hook, M. (1990). *Bacteriodes gingivalis* and *Bacteriodes intermedius* recognize different sites on human fibrinogen. J. Bacteriol. 172, 716–726.

Lee, C. Y., Buranem, S. L. and Ye, Z-H. (1991). Construction of single copy integration vectors for *Staphylococcus aureus*. Gene 103:101–105.

McDevitt, D., Vaudaux P. and Foster, T. J. (1992). Genetic evidence that bound coagulase of *Staphylococcus aureus* is not clumping factor. Infect. Immun. 60:1514–1523.

McDevitt, D., Francois, P., Vaudaux, P. and Foster T. J. (1994). Molecular characterization of the fibrinogen receptor (clumping factor) of *Staphylococcus aureus*. Molec. Microbiol. 11, 237–248.

Maki, D. G. (1982). Infections associated with intravascular lines. In Current topics in infectious diseases, Vol 3 Remington J. S., and Swartz, M. N. (eds.). McGraw Hill, New York, pp. 309–363.

Nowicki, B., Rhen, M., Vaisanen-Rhen, V., Pere, A. and Korhonen, T. K. (1984). Immunofluorescence study of fimbrial phase variation in *Escherichia coli* KS71. J. Bacteriol. 160, 691–695.

Patel, A. H., Nowlan, P. Weavers, E. D. and Foster, T. J. (1987). Virulence of protein A-deficient and alpha toxin-deficient mutants of *Staphylococcus aureus* isolated by allelic-replacement. Infect. Immun. 55, 3103–3110.

Patti, J. M., Jonsson, H., Guss, B., Switalski, L. M., Wiberg, K., Lindberg, M. and Hook M. (1992). Molecular characterization and expression of a gene encoding a *Staphylococcus aureus* collagen adhesin. J. Biol. Chem. 267, 4766–772.

Schneewind, O., Mihaylova, D. and Model, P. (1993). Cell wall sorting signals in surface proteins of Gram-positive bacteria. EMBO J. 12, 4803–4811.

Signas, C., Raucci, G., Jonsson, K., Lindgren, P. E., Anantharamaiah, G. M., Hook, M. and Lindberg, M. (1989). Nucleotide sequence of the gene for a fibronectin-binding protein from *Staphylococcus aureus*: use of this peptide sequence in the synthesis of biologically active peptides. Proc. Natl. Acad. Sci. USA 86:699–703.

Switalski, L. M. (1976). Isolation and purification of staphylococcal clumping factor. In Staphylococci and staphylococcal diseases. Jeliaszewicz, J. (ed.) Gustav Fischer Verlag, Stuttgart, pp. 413–425.

Tomich, P. K., An, F. Y, and Clewell, D. B. (1980). Properties of erythromycin inducible transposon Tn917 in *Streptococcus faecalis*. J. Bacteriol. 141, 1366–1374.

Usui, Y. (1986). Biochemical properties of fibrinogen binding protein (clumping factor) of the staphylococcal cell surface. 26L. Bakt. Hyg. A262, 287–297.

Vaudaux, P., Pittet, D., Haeberli, A., Huggler, E., Nydegger, U. E., Lew, D. P. and Waldvogel, F. A. (1989). Host factors selectively increase staphylococcal adherence on inserted catheters. A role for fibronectin and fibrinogen or fibrin. J. Infect. Dis. 160, 865–875.

Vaudaux, P., Proctor, R. A., McDevitt, D., Foster, T. J., Lew, D. P., Wabers, H. and S. Cooper. (1991). Use of adherence defective mutants of *Staphylococcus aureus* (SA) to identify adherence promoting proteins deposited from profusing blood in a canine shunt model. Program Abstr. 31st Intersci. Conf. Antimicrobiol. Agents Chemother., abst 1068.

Vaudaux, P., Pittet, D., Haeberli, H., Lerch, P. G., Morgenthaler, J. J., Proctor, R. A., Waldvogel, F. A. and Lew, D. P. (1993). Fibronectin is more active than fibrin or fibrinogen in promoting *Staphylococcus aureus* adherence to inserted intravascular devices. J. Infect. Dis. 167, 633–641.

Yanisch-Perron, C., Veira, J. C. and Messing, J. (1985). Improved M13 phage cloning vectors and host strains: nucleotide sequences of the M13 mpl8 and pUC19 vectors. Gene 33:103–119.

Youngman, P. (1985). Plasmid vectors for recovering and exploiting Tn917 transpositions in Bacillus and other Gram-positives. In Plasmids: a practical approach. Hardy, K. (ed.), IRL Press, Oxford, pp. 79–103.

What is claimed is:

1. An isolated antibody capable of specifically binding to an *S. aureus* fibrinogen binding protein encoded by a DNA molecule consisting of Sequence ID No. 1 or degenerates thereof.

2. An isolated antibody according to claim 1 wherein said antibody is a monoclonal antibody.

3. An isolated antibody according to claim 1 wherein said antibody is a polyclonal antibody.

4. An isolated antibody capable of specifically binding to an *S. aureus* fibrinogen binding protein which is expressed by a microorganism which has been transformed with plasmid pCF3, Accession No. 40959, which is deposited at the NCIMB in Aberdeen, Scotland.

5. An isolated antibody capable of specifically binding to an *S. aureus* fibrinogen binding protein which is expressed by a microorganism which has been transformed with plasmid pCF10, Accession No. 40674, which is deposited at the NCIMB in Aberdeen Scotland.

6. An isolated antibody capable of specifically binding to a fibrinogen binding protein selected from the group consisting of amino acids 23 to 550 of Sequence ID No. 2, 332 to 550 of Sequence ID No. 2, and 332 to 425 of Sequence ID No. 2.

7. Isolated antisera capable of specifically binding to an *S. aureus* fibrinogen binding protein encoded by a DNA molecule consisting of Sequence ID No. 1 or degenerates thereof.

8. An isolated antibody according to claim 6 wherein said antibody is a monoclonal antibody.

9. An isolated antibody according to claim 6 wherein said antibody is a polyclonal antibody.

* * * * *

SEQUENCE LISTING

<160> NUMBER OF SEQ ID NOS: 20

<210> SEQ ID NO 1
<211> LENGTH: 3498
<212> TYPE: DNA
<213> ORGANISM: Staphylococcus aureus
<220> FEATURE:
<221> NAME/KEY: CDS
<222> LOCATION: (301)..(3099)

<400> SEQUENCE: 1

```
ggtaccataa attacacatc tgcttttgaa aaatatgat ttcaagctag gattacatta        60
ggtagagttc atattaataa taaaaaatgt ttgcaatcaa atcgtacgtt gtcgtttgta       120
attcttaaaa tagcaataaa taaatgtttt gttagtaaag tattattgtg gataataaaa       180
tatcgataca aattaattgc tataatgcaa ttttagtgta taattccatt aacagagatt       240
aaatatatct taagggtat atagttaata taaaatgact ttttaaaaag agggaataaa        300
```

| | | | | | | | | | | | | | | | | |
|---|---|---|---|---|---|---|---|---|---|---|---|---|---|---|---|---|
| atg | aat | atg | aag | aaa | aaa | gaa | aaa | cac | gca | att | cgg | aaa | aaa | tcg | att | 348 |
| Met | Asn | Met | Lys | Lys | Lys | Glu | Lys | His | Ala | Ile | Arg | Lys | Lys | Ser | Ile | |
| 1 | | | | 5 | | | | | 10 | | | | | 15 | | |

| ggc | gtg | gct | tca | gtg | ctt | gta | ggt | acg | tta | atc | ggt | ttt | gga | cta | ctc | 396 |
|---|---|---|---|---|---|---|---|---|---|---|---|---|---|---|---|---|
| Gly | Val | Ala | Ser | Val | Leu | Val | Gly | Thr | Leu | Ile | Gly | Phe | Gly | Leu | Leu | |
| | | | 20 | | | | | 25 | | | | | 30 | | | |

| agc | agt | aaa | gaa | gca | gat | gca | agt | gaa | aat | agt | gtt | acg | caa | tct | gat | 444 |
|---|---|---|---|---|---|---|---|---|---|---|---|---|---|---|---|---|
| Ser | Ser | Lys | Glu | Ala | Asp | Ala | Ser | Glu | Asn | Ser | Val | Thr | Gln | Ser | Asp | |
| | | 35 | | | | | 40 | | | | | 45 | | | | |

| agc | gca | agt | aac | gaa | agc | aaa | agt | aat | gat | tca | agt | agc | gtt | agt | gct | 492 |
|---|---|---|---|---|---|---|---|---|---|---|---|---|---|---|---|---|
| Ser | Ala | Ser | Asn | Glu | Ser | Lys | Ser | Asn | Asp | Ser | Ser | Ser | Val | Ser | Ala | |
| 50 | | | | | 55 | | | | | 60 | | | | | | |

| gca | cct | aaa | aca | gac | gac | aca | aac | gtg | agt | gat | act | aaa | aca | tcg | tca | 540 |
|---|---|---|---|---|---|---|---|---|---|---|---|---|---|---|---|---|
| Ala | Pro | Lys | Thr | Asp | Asp | Thr | Asn | Val | Ser | Asp | Thr | Lys | Thr | Ser | Ser | |
| 65 | | | | | 70 | | | | | 75 | | | | | 80 | |

| aac | act | aat | aat | ggc | gaa | acg | agt | gtg | gcg | caa | aat | cca | gca | caa | cag | 588 |
|---|---|---|---|---|---|---|---|---|---|---|---|---|---|---|---|---|
| Asn | Thr | Asn | Asn | Gly | Glu | Thr | Ser | Val | Ala | Gln | Asn | Pro | Ala | Gln | Gln | |
| | | | | 85 | | | | | 90 | | | | | 95 | | |

| gaa | acg | aca | caa | tca | tca | tca | aca | aat | gca | act | acg | gaa | gaa | acg | ccg | 636 |
|---|---|---|---|---|---|---|---|---|---|---|---|---|---|---|---|---|
| Glu | Thr | Thr | Gln | Ser | Ser | Ser | Thr | Asn | Ala | Thr | Thr | Glu | Glu | Thr | Pro | |
| | | | 100 | | | | | 105 | | | | | 110 | | | |

| gta | act | ggt | gaa | gct | act | act | acg | aca | acg | aat | caa | gct | aat | aca | ccg | 684 |
|---|---|---|---|---|---|---|---|---|---|---|---|---|---|---|---|---|
| Val | Thr | Gly | Glu | Ala | Thr | Thr | Thr | Thr | Thr | Asn | Gln | Ala | Asn | Thr | Pro | |
| | | | 115 | | | | | 120 | | | | | 125 | | | |

| gca | aca | act | caa | tca | agc | aat | aca | aat | gcg | gag | gaa | tta | gtg | aat | caa | 732 |
|---|---|---|---|---|---|---|---|---|---|---|---|---|---|---|---|---|
| Ala | Thr | Thr | Gln | Ser | Ser | Asn | Thr | Asn | Ala | Glu | Glu | Leu | Val | Asn | Gln | |
| | 130 | | | | | 135 | | | | | 140 | | | | | |

| aca | agt | aat | gaa | acg | act | ttt | aat | gat | act | aat | aca | gta | tca | tct | gta | 780 |
|---|---|---|---|---|---|---|---|---|---|---|---|---|---|---|---|---|
| Thr | Ser | Asn | Glu | Thr | Thr | Phe | Asn | Asp | Thr | Asn | Thr | Val | Ser | Ser | Val | |
| 145 | | | | | 150 | | | | | 155 | | | | | 160 | |

| aat | tca | cct | caa | aat | tct | aca | aat | gcg | gaa | aat | gtt | tca | aca | acg | caa | 828 |
|---|---|---|---|---|---|---|---|---|---|---|---|---|---|---|---|---|
| Asn | Ser | Pro | Gln | Asn | Ser | Thr | Asn | Ala | Glu | Asn | Val | Ser | Thr | Thr | Gln | |
| | | | | 165 | | | | | 170 | | | | | 175 | | |

| gat | act | tca | act | gaa | gca | aca | cct | tca | aac | aat | gaa | tca | gct | cca | cag | 876 |
|---|---|---|---|---|---|---|---|---|---|---|---|---|---|---|---|---|
| Asp | Thr | Ser | Thr | Glu | Ala | Thr | Pro | Ser | Asn | Asn | Glu | Ser | Ala | Pro | Gln | |
| | | | 180 | | | | | 185 | | | | | 190 | | | |

| agt | aca | gat | gca | agt | aat | aaa | gat | gta | gtt | aat | caa | gcg | gtt | aat | aca | 924 |
|---|---|---|---|---|---|---|---|---|---|---|---|---|---|---|---|---|
| Ser | Thr | Asp | Ala | Ser | Asn | Lys | Asp | Val | Val | Asn | Gln | Ala | Val | Asn | Thr | |
| | | 195 | | | | | 200 | | | | | 205 | | | | |

-continued

```
agt gcg cct aga atg aga gca ttt agt tta gcg gca gta gct gca gat         972
Ser Ala Pro Arg Met Arg Ala Phe Ser Leu Ala Ala Val Ala Ala Asp
    210             215                 220 gca ccg gca gct ggc aca gat att acg aat cag ttg acg aat gtg aca        1020
Ala Pro Ala Ala Gly Thr Asp Ile Thr Asn Gln Leu Thr Asn Val Thr
225             230                 235                 240 gtt ggt att gac tct ggt acg act gtg tat ccg cac caa gca ggt tat        1068
Val Gly Ile Asp Ser Gly Thr Thr Val Tyr Pro His Gln Ala Gly Tyr
                245                 250                 255 gtc aaa ctg aat tat ggt ttt tca gtg cct aat tct gct gtt aaa ggt        1116
Val Lys Leu Asn Tyr Gly Phe Ser Val Pro Asn Ser Ala Val Lys Gly
            260                 265                 270 gac aca ttc aaa ata act gta cct aaa gaa tta aac tta aat ggt gta        1164
Asp Thr Phe Lys Ile Thr Val Pro Lys Glu Leu Asn Leu Asn Gly Val
        275                 280                 285 act tca act gct aaa gtg cca cca att atg gct gga gat caa gta ttg        1212
Thr Ser Thr Ala Lys Val Pro Pro Ile Met Ala Gly Asp Gln Val Leu
290                 295                 300 gca aat ggt gta atc gat agt gat ggt aat gtt att tat aca ttt aca        1260
Ala Asn Gly Val Ile Asp Ser Asp Gly Asn Val Ile Tyr Thr Phe Thr
305                 310                 315                 320 gac tat gta aat act aaa gat gat gta aaa gca act ttg acc atg ccc        1308
Asp Tyr Val Asn Thr Lys Asp Asp Val Lys Ala Thr Leu Thr Met Pro
                325                 330                 335 gct tat att gac cct gaa aat gtt aaa aag aca ggt aat gtg aca ttg        1356
Ala Tyr Ile Asp Pro Glu Asn Val Lys Lys Thr Gly Asn Val Thr Leu
            340                 345                 350 gct act ggc ata ggt agt aca aca gca aac aaa aca gta tta gta gat        1404
Ala Thr Gly Ile Gly Ser Thr Thr Ala Asn Lys Thr Val Leu Val Asp
        355                 360                 365 tat gaa aaa tat ggt aag ttt tat aac tta tct att aaa ggt aca att        1452
Tyr Glu Lys Tyr Gly Lys Phe Tyr Asn Leu Ser Ile Lys Gly Thr Ile
370                 375                 380 gac caa atc gat aaa aca aat aat acg tat cgt cag aca att tat gtc        1500
Asp Gln Ile Asp Lys Thr Asn Asn Thr Tyr Arg Gln Thr Ile Tyr Val
385                 390                 395                 400 aat cca agt gga gat aac gtt att gcg ccg gtt tta aca ggt aat tta        1548
Asn Pro Ser Gly Asp Asn Val Ile Ala Pro Val Leu Thr Gly Asn Leu
                405                 410                 415 aaa cca aat acg gat agt aat gca tta ata gat cag caa aat aca agt        1596
Lys Pro Asn Thr Asp Ser Asn Ala Leu Ile Asp Gln Gln Asn Thr Ser
            420                 425                 430 att aaa gta tat aaa gta gat aat gca gct gat tta tct gaa agt tac        1644
Ile Lys Val Tyr Lys Val Asp Asn Ala Ala Asp Leu Ser Glu Ser Tyr
        435                 440                 445 ttt gtg aat cca gaa aac ttt gag gat gtc act aat agt gtg aat att        1692
Phe Val Asn Pro Glu Asn Phe Glu Asp Val Thr Asn Ser Val Asn Ile
450                 455                 460 aca ttc cca aat cca aat caa tat aaa gta gag ttt aat acg cct gat        1740
Thr Phe Pro Asn Pro Asn Gln Tyr Lys Val Glu Phe Asn Thr Pro Asp
465                 470                 475                 480 gat caa att aca aca ccg tat ata gta gtt gtt aat ggt cat att gat        1788
Asp Gln Ile Thr Thr Pro Tyr Ile Val Val Val Asn Gly His Ile Asp
                485                 490                 495 ccg aat agc aaa ggt gat tta gct tta cgt tca act tta tat ggg tat        1836
Pro Asn Ser Lys Gly Asp Leu Ala Leu Arg Ser Thr Leu Tyr Gly Tyr
            500                 505                 510 aac tcg aat ata att tgg cgc tct atg tca tgg gac aac gaa gta gca        1884
Asn Ser Asn Ile Ile Trp Arg Ser Met Ser Trp Asp Asn Glu Val Ala
        515                 520                 525
```

-continued

| | | |
|---|---|---|
| ttt aat aac gga tca ggt tct ggt gac ggt atc gat aaa cca gtt gtt<br>Phe Asn Asn Gly Ser Gly Ser Gly Asp Gly Ile Asp Lys Pro Val Val<br>530                          535                          540 | 1932 | |
| cct gaa caa cct gat gag cct ggt gaa att gaa cca att cca gag gat<br>Pro Glu Gln Pro Asp Glu Pro Gly Glu Ile Glu Pro Ile Pro Glu Asp<br>545                        550                        555                        560 | 1980 | |
| tca gat tct gac cca ggt tca gat tct ggc agc gat tct aat tca gat<br>Ser Asp Ser Asp Pro Gly Ser Asp Ser Gly Ser Asp Ser Asn Ser Asp<br>                        565                          570                        575 | 2028 | |
| agc ggt tca gat tcg ggt agt gat tct aca tca gat agt ggt tca gat<br>Ser Gly Ser Asp Ser Gly Ser Asp Ser Thr Ser Asp Ser Gly Ser Asp<br>            580                        585                        590 | 2076 | |
| tca gcg agt gat tca gat tca gca agt gat tca gac tca gcg agt gat<br>Ser Ala Ser Asp Ser Asp Ser Ala Ser Asp Ser Asp Ser Ala Ser Asp<br>595                          600                        605 | 2124 | |
| tca gat tca gca agc gat tcc gac tca gcg agc gat tcc gac tca gac<br>Ser Asp Ser Ala Ser Asp Ser Asp Ser Ala Ser Asp Ser Asp Ser Asp<br>            610                        615                        620 | 2172 | |
| aat gac tcg gat tca gat agc gat tct gac tca gac agt gac tca gat<br>Asn Asp Ser Asp Ser Asp Ser Asp Ser Asp Ser Asp Ser Asp Ser Asp<br>625                          630                        635                        640 | 2220 | |
| tcc gac agt gac tca gat tca gat agc gat tct gac tca gac agt gac<br>Ser Asp Ser Asp Ser Asp Ser Asp Ser Asp Ser Asp Ser Asp Ser Asp<br>                        645                        650                        655 | 2268 | |
| tca gat tca gat agc gat tca gat tca gat agc gat tca gat tcc gac<br>Ser Asp Ser Asp Ser Asp Ser Asp Ser Asp Ser Asp Ser Asp Ser Asp<br>            660                        665                        670 | 2316 | |
| agt gat tcc gac tca gac agc gat tct gac tcc gac agt gat tcc gac<br>Ser Asp Ser Asp Ser Asp Ser Asp Ser Asp Ser Asp Ser Asp Ser Asp<br>                        675                        680                        685 | 2364 | |
| tca gac agc gat tca gat tcc gac agt gat tcc gac tca gat agc gat<br>Ser Asp Ser Asp Ser Asp Ser Asp Ser Asp Ser Asp Ser Asp Ser Asp<br>            690                        695                        700 | 2412 | |
| tcc gac tca gat agc gac tca gat tca gac agc gat tca gat tca gac<br>Ser Asp Ser Asp Ser Asp Ser Asp Ser Asp Ser Asp Ser Asp Ser Asp<br>705                          710                        715                        720 | 2460 | |
| agc gat tca gat tca gat agc gat tca gat tcc gac agt gac tca gat<br>Ser Asp Ser Asp Ser Asp Ser Asp Ser Asp Ser Asp Ser Asp Ser Asp<br>                        725                        730                        735 | 2508 | |
| tcc gac agt gac tcg gat tca gat agc gat tca gat tcc gac agt gac<br>Ser Asp Ser Asp Ser Asp Ser Asp Ser Asp Ser Asp Ser Asp Ser Asp<br>            740                        745                        750 | 2556 | |
| tca gat tcc gac agt gac tca gac tca gac agt gat tcg gat tca gcg<br>Ser Asp Ser Asp Ser Asp Ser Asp Ser Asp Ser Asp Ser Asp Ser Ala<br>                        755                        760                        765 | 2604 | |
| agt gat tcg gat tca gat agt gat tcc gac tcc gac agt gac tcg gat<br>Ser Asp Ser Asp Ser Asp Ser Asp Ser Asp Ser Asp Ser Asp Ser Asp<br>            770                        775                        780 | 2652 | |
| tca gat agc gac tca gac tcg gat agc gac tcg gat tca gat agc gat<br>Ser Asp Ser Asp Ser Asp Ser Asp Ser Asp Ser Asp Ser Asp Ser Asp<br>785                          790                        795                        800 | 2700 | |
| tcg gac tca gat agc gat tca gaa tca gac agc gat tca gaa tca gac<br>Ser Asp Ser Asp Ser Asp Ser Glu Ser Asp Ser Asp Ser Glu Ser Asp<br>                        805                        810                        815 | 2748 | |
| agc gat tca gat tca gac agc gac tca gac agt gac tca gat tca gat<br>Ser Asp Ser Asp Ser Asp Ser Asp Ser Asp Ser Asp Ser Asp Ser Asp<br>            820                        825                        830 | 2796 | |
| agt gac tcg gat tca gcg agt gat tca gac tca ggt agt gac tcc gat<br>Ser Asp Ser Asp Ser Ala Ser Asp Ser Asp Ser Gly Ser Asp Ser Asp<br>            835                        840                        845 | 2844 | |

-continued

| | | | | | | | | | | | | | | |
|---|---|---|---|---|---|---|---|---|---|---|---|---|---|---|
| tca | tca | agt | gat | tcc | gac | tca | gaa | agt | gat | tca | aat | agc | gat tcc gag | 2892 |
| Ser | Ser | Ser | Asp | Ser | Asp | Ser | Glu | Ser | Asp | Ser | Asn | Ser | Asp Ser Glu | |
| | 850 | | | | 855 | | | | 860 | | | | | |
| tca | ggt | tct | aac | aat | aat | gta | gtt | ccg | cct | aat | tca | cct | aaa aat ggt | 2940 |
| Ser | Gly | Ser | Asn | Asn | Asn | Val | Val | Pro | Pro | Asn | Ser | Pro | Lys Asn Gly | |
| 865 | | | | 870 | | | | | 875 | | | | 880 | |
| act | aat | gct | tct | aat | aaa | aat | gag | gct | aaa | gat | agt | aaa | gaa cca tta | 2988 |
| Thr | Asn | Ala | Ser | Asn | Lys | Asn | Glu | Ala | Lys | Asp | Ser | Lys | Glu Pro Leu | |
| | | | | 885 | | | | | 890 | | | | 895 | |
| cca | gat | aca | ggt | tct | gaa | gat | gaa | gca | aat | acg | tca | cta | att tgg gga | 3036 |
| Pro | Asp | Thr | Gly | Ser | Glu | Asp | Glu | Ala | Asn | Thr | Ser | Leu | Ile Trp Gly | |
| | | 900 | | | | | 905 | | | | | 910 | | |
| tta | tta | gca | tca | ata | ggt | tca | tta | cta | ctt | ttc | aga | aga | aaa aaa gaa | 3084 |
| Leu | Leu | Ala | Ser | Ile | Gly | Ser | Leu | Leu | Leu | Phe | Arg | Arg | Lys Lys Glu | |
| | 915 | | | | | 920 | | | | | 925 | | | |
| aat | aaa | gat | aag | aaa | taagtaataa tgatattaaa ttaatcatat gattcatgaa | | | | | | | | | 3139 |
| Asn | Lys | Asp | Lys | Lys | | | | | | | | | | |
| | 930 | | | | | | | | | | | | | | gaagccacct taaaaggtgc ttctttact tggattttcc aaatatattg tttgaatata 3199
attaataatt aattcatcaa cagttaatta ttttaaaaag gtagatgtta tataatttgg 3259
cttggcgaaa aaataggtg taaggtaggt tgttaattag ggaaaattaa ggagaaaata 3319
cagttgaaaa ataaattgct agttttatca ttgggagcat tatgtgtatc acaaatttgg 3379
gaaagtaatc gtgcgagtgc agtggtttct ggggagaaga atccatatgt atctgagtcg 3439
ttgaaactga ctaataataa aaataaatct agaacagtag aagagtataa gaaaagctt 3498

<210> SEQ ID NO 2
<211> LENGTH: 933
<212> TYPE: PRT
<213> ORGANISM: Staphylococcus aureus

<400> SEQUENCE: 2

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

```
Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
        210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
        290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
                355                 360                 365

Tyr Glu Lys Tyr Gly Lys Phe Tyr Asn Leu Ser Ile Lys Gly Thr Ile
        370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
                420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
        450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
                500                 505                 510

Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
        530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
                580                 585                 590

Ser Ala Ser Asp Ser Asp Ser Ala Ser Asp Ser Asp Ser Ala Ser Asp
                595                 600                 605
```

-continued

Ser Asp Ser Ala Ser Asp Ser Asp Ala Ser Asp Ser Asp
    610                 615                 620

Asn Asp Ser Asp Ser Asp Ser Asp Ser Asp Ser Ser Asp
625                 630                 635                 640

Ser Asp Ser Asp Ser Asp Ser Asp Ser Asp Ser Asp Ser Asp
            645                 650                 655

Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Ala
            755                 760                 765

Ser Asp Ser Asp Ser Asp Ser Asp Ser Asp Ser Asp Ser Asp
770                 775                 780

Ser Asp Ser Asp Ser Asp Ser Asp Ser Asp Ser Asp Ser Asp
785                 790                 795                 800

Ser Asp Ser Asp Ser Glu Ser Asp Ser Asp Ser Glu Ser Asp
            805                 810                 815

Ser Asp Ser Asp Ser Asp Ser Asp Ser Asp Ser Asp Ser Asp
            820                 825                 830

Ser Asp Ser Asp Ser Ala Ser Asp Ser Gly Ser Asp Ser Asp
            835                 840                 845

Ser Ser Ser Asp Ser Asp Ser Glu Ser Asp Ser Asn Ser Asp Ser Glu
850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
            915                 920                 925

Asn Lys Asp Lys Lys
    930

<210> SEQ ID NO 3
<211> LENGTH: 12
<212> TYPE: PRT
<213> ORGANISM: Staphylococcus aureus

<400> SEQUENCE: 3

Gly Thr Ile Asn Tyr Thr Ser Ala Phe Glu Lys Ile
 1               5                  10

<210> SEQ ID NO 4
<211> LENGTH: 58
<212> TYPE: PRT
<213> ORGANISM: Staphylococcus aureus -continued

```
<400> SEQUENCE: 4

Phe Gln Ala Arg Ile Thr Leu Gly Arg Val His Ile Asn Asn Lys Lys
 1               5                  10                  15

Cys Leu Gln Ser Asn Arg Thr Leu Ser Phe Val Ile Leu Lys Ile Ala
                20                  25                  30

Ile Asn Lys Met Phe Val Ser Lys Val Leu Leu Trp Ile Ile Lys Tyr
         35                  40                  45

Arg Tyr Lys Leu Ile Ala Ile Met Gln Phe
     50                  55

<210> SEQ ID NO 5
<211> LENGTH: 15
<212> TYPE: PRT
<213> ORGANISM: Staphylococcus aureus

<400> SEQUENCE: 5

Cys Ile Ile Pro Leu Thr Glu Ile Lys Tyr Ile Leu Lys Gly Ile
 1               5                  10                  15

<210> SEQ ID NO 6
<211> LENGTH: 6
<212> TYPE: PRT
<213> ORGANISM: Staphylococcus aureus

<400> SEQUENCE: 6

Val Ile Met Ile Leu Asn
 1               5

<210> SEQ ID NO 7
<211> LENGTH: 21
<212> TYPE: PRT
<213> ORGANISM: Staphylococcus aureus

<400> SEQUENCE: 7

Arg Ser His Leu Lys Arg Cys Phe Phe Tyr Leu Asp Phe Pro Asn Ile
 1               5                  10                  15

Leu Phe Glu Tyr Asn
             20

<210> SEQ ID NO 8
<211> LENGTH: 11
<212> TYPE: PRT
<213> ORGANISM: Staphylococcus aureus

<400> SEQUENCE: 8

Leu Ile His Gln Gln Leu Ile Ile Leu Lys Arg
 1               5                  10

<210> SEQ ID NO 9
<211> LENGTH: 12
<212> TYPE: PRT
<213> ORGANISM: Staphylococcus aureus

<400> SEQUENCE: 9

Met Leu Tyr Asn Leu Ala Trp Arg Lys Asn Arg Val
 1               5                  10

<210> SEQ ID NO 10
<211> LENGTH: 8
<212> TYPE: PRT
<213> ORGANISM: Staphylococcus aureus
```

-continued

```
<400> SEQUENCE: 10

Gly Arg Leu Leu Ile Arg Glu Asn
 1               5

<210> SEQ ID NO 11
<211> LENGTH: 7
<212> TYPE: PRT
<213> ORGANISM: Staphylococcus aureus

<400> SEQUENCE: 11

Gly Glu Asn Thr Val Glu Lys
 1               5

<210> SEQ ID NO 12
<211> LENGTH: 17
<212> TYPE: PRT
<213> ORGANISM: Staphylococcus aureus

<400> SEQUENCE: 12

Ile Ala Ser Phe Ile Ile Gly Ser Ile Met Cys Ile Thr Asn Leu Gly
 1               5                  10                  15

Lys

<210> SEQ ID NO 13
<211> LENGTH: 15
<212> TYPE: PRT
<213> ORGANISM: Staphylococcus aureus

<400> SEQUENCE: 13

Ser Cys Glu Cys Ser Gly Phe Trp Gly Glu Glu Ser Ile Cys Ile
 1               5                  10                  15

<210> SEQ ID NO 14
<211> LENGTH: 5
<212> TYPE: PRT
<213> ORGANISM: Staphylococcus aureus

<400> SEQUENCE: 14

Val Val Glu Thr Asp
 1               5

<210> SEQ ID NO 15
<211> LENGTH: 5
<212> TYPE: PRT
<213> ORGANISM: Staphylococcus aureus

<400> SEQUENCE: 15

Asn Ser Arg Arg Val
 1               5

<210> SEQ ID NO 16
<211> LENGTH: 16
<212> TYPE: PRT
<213> ORGANISM: Staphylococcus aureus

<400> SEQUENCE: 16

Ser Asp Ser Asp Ser Asp Ser Asp Ser Asp Ser Asp Gly Gly Gly Cys
 1               5                  10                  15

<210> SEQ ID NO 17
<211> LENGTH: 10
<212> TYPE: PRT
<213> ORGANISM: Staphylococcus aureus
```

-continued

```
<400> SEQUENCE: 17

Val Gly Thr Leu Ile Gly Phe Gly Leu Leu
  1               5                  10

<210> SEQ ID NO 18
<211> LENGTH: 7
<212> TYPE: PRT
<213> ORGANISM: Staphylococcus aureus

<400> SEQUENCE: 18

Gly Lys Ile Ile Gly Ile Asp
  1               5

<210> SEQ ID NO 19
<211> LENGTH: 16
<212> TYPE: PRT
<213> ORGANISM: Staphylococcus aureus

<400> SEQUENCE: 19

Met Asn Gln Thr Ser Asn Glu Thr Thr Phe Asn Asp Thr Asn Thr Val
  1               5                  10                  15

<210> SEQ ID NO 20
<211> LENGTH: 18
<212> TYPE: PRT
<213> ORGANISM: Staphylococcus aureus

<400> SEQUENCE: 20

Ala Val Ala Ala Asp Ala Pro Ala Ala Gly Thr Asp Ile Thr Asn Gln
  1               5                  10                  15

Leu Thr
```